(12) United States Patent
Adang

(10) Patent No.: US 6,410,684 B1
(45) Date of Patent: Jun. 25, 2002

(54) SERINE PROTEASE INHIBITORS

(75) Inventor: Anton Egbert Peter Adang, Eindhoven (NL)

(73) Assignee: Akzo Nobel N.V., Arhnhem (NL)

( * ) Notice: Subject to any disclaimer, the term of this patent is extended or adjusted under 35 U.S.C. 154(b) by 0 days.

(21) Appl. No.: 09/142,110

(22) PCT Filed: Feb. 26, 1997

(86) PCT No.: PCT/EP97/00938

§ 371 (c)(1),
(2), (4) Date: Sep. 1, 1998

(87) PCT Pub. No.: WO97/31937

PCT Pub. Date: Sep. 4, 1997

(30) Foreign Application Priority Data

Mar. 1, 1996 (EP) ............................................ 96200543

(51) Int. Cl.⁷ ................................................. C07K 5/08
(52) U.S. Cl. .......................... 530/331; 530/330; 514/18; 514/19; 544/1
(58) Field of Search ...................... 514/18, 19; 530/330, 530/331; 544/1

(56) References Cited

U.S. PATENT DOCUMENTS 4,556,655 A * 12/1985 Andrews et al. ............. 514/222

FOREIGN PATENT DOCUMENTS

| EP | 0408371 | 1/1991 |
|---|---|---|
| EP | 0672658 | 9/1995 |
| EP | 0686642 | 12/1995 |
| WO | WO 9425051 | 11/1994 |
| WO | WO 9429336 | 12/1994 |
| WO | WO 9523608 | 9/1995 |
| WO | WO 9535311 | 12/1995 |
| WO | WO 9619483 | 6/1996 |

OTHER PUBLICATIONS

Database WPI, Week 9613, XP002031054, Jan. 23, 1996.

Costanzo et al., *Journal of Medicinal Chemistry*, 39:16:3039–3043, 1996.

Jones et al., *Letters in Peptide Science*, 2:147–154, 1995.

* cited by examiner

*Primary Examiner*—Christopher S. F. Low
(74) *Attorney, Agent, or Firm*—William M. Blackstone

(57) ABSTRACT

Serine protease inhibitors, prodrugs thereof and pharmaceutically acceptable salts thereof are disclosed. The serine protease inhibitors exhibit anticoagulant activity and are useful for treating or preventing thrombin related diseases.

17 Claims, No Drawings

SERINE PROTEASE INHIBITORS

FIELD OF THE INVENTION

The invention relates to a serine protease inhibitor having an alkynylamino side chain, a pharmaceutical composition containing the same, as well as the use of said inhibitor for the manufacture of a medicament for treating and preventing thrombin-related diseases.

BACKGROUND OF THE INVENTION

Serine proteases are enzymes which, amongst other things, play an important role in the blood coagulation cascade. Members of this group of proteases are for example thrombin, trypsin, factors VIIa, IXa, Xa, XIa, XIIa, and protein C. Thrombin is the serine protease which regulates the last step in the coagulation cascade. The prime function of thrombin is the cleavage of fibrinogen to generate fibrin monomers, which form an insoluble gel by cross-linking. In addition, thrombin regulates its own production by activating factors V and VIII earlier in the cascade. It also has important actions at cellular level, where it acts on specific receptors to cause platelet aggregation, endothelial cell activation and fibroblast proliferation. Thus thrombin has a central regulatory role in haemostasis and thrombus formation. Since inhibitors of thrombin may have a wide range of therapeutical applications, extensive research has been performed in this area. In the development of synthetic inhibitors of serine proteases, and more specifically of thrombin, the interest in small synthetic peptides that are recognized by proteolytic enzymes in a manner similar to that of natural substrates, has increased. As a result, new peptide-like inhibitors have been prepared, such as the transition state inhibitors of thrombin. The search for more effective and more selective thrombin inhibitors continues unabated in order to obtain thrombin inhibitors which can be administered in lower dosages and which have fewer and less severe side effects. Furthermore, special attention is paid to oral bioavailability. Potent intravenous thrombin inhibitors are clinically effective in acute care settings requiring the treatment of thrombin-related diseases. However, particularly the prevention of thrombin-related diseases such as myocardial infarct, thrombosis and stroke require long-term therapy, preferably by orally dosing an anticoagulant.

Most of the peptide-like thrombin inhibitors disclosed in prior publications contain side chains of arginine. The thrombin inhibitors may also contain lysine side chains instead of arginine, such as the inhibitor N-Me-D-Cha-Pro-Lys-COOH and derivatives thereof, disclosed by Jones et al., J. Enzyme Inhibition, 9 (1995), 43–60, and the inhibitors N-Me-D-Phe-Pro-Lys-X, X being a carboxamide or carboxylic acid, disclosed by Lewis et al., Thrombosis and Haemostasis, 74(4) (1995), 1107–12. In addition, Brady et al., Bioorganic & Medical Chemistry, 3 (1995), 1063–78, describe a D-Phe-Pro-Lys-ketoester. Other thrombin inhibitors are disclosed in WO 94/25051 wherein the lysine or arginine side chain is replaced by aminocyclohexyl moieties. A problem of the known arginine and lysine containing thrombin inhibitors is that they have low oral bioavailability.

SUMMARY OF THE INVENTION

It has now been found that serine protease inhibitors, and in particular thrombin, Xa and VIIa inhibitors, having an alkynylamino side chain, according to the formula I

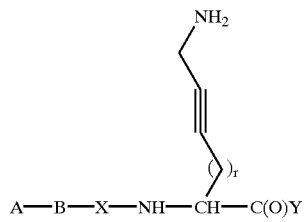

wherein
A is H, optionally substituted D,L α-hydroxyacetyl, $R^1$, $R^1$—O—C(O)—, $R^1$—C(O)—, $R^1$—$SO_2$—, $R^2OOC$—$(CHR^2)_m$—$SO_2$—, $R^2OOC$—$(CHR^2)_m$—, $H_2NCO$—$(CHR^2)_m$—, or an N-protecting group, wherein $R^1$ is selected from (1–12C)alkyl, (2–12C) alkenyl, (2–12C)alkynyl and (3–8C)cycloalkyl, which groups may optionally be substituted with (3–8C) cycloalkyl, (1–6C)alkoxy, oxo, OH, COOH, $CF_3$ or halogen, and from (6–14C)aryl, (7–15C)aralkyl and (8–16C)aralkenyl, the aryl groups of which may optionally be substituted with (1–6C)alkyl, (3–8C)cycloalkyl, (1–6C)alkoxy, OH, COOH, $CF_3$ or halogen; each group $R^2$ is independently H or has the same meaning as $R^1$; m is 1, 2 or 3;

B is a bond, an amino acid of the formula —NH—CH $[(CH_2)_pC(O)OH]$—C(O)— or an ester derivative thereof with p being 0, 1, 2 or 3, —N((1–12C)alkyl)-$CH_2$—CO—, —N((2–12C)alkenyl)-$CH_2$—CO—, —N((2–12C)alkynyl)-$CH_2$—CO—, -N(benzyl)-$CH_2$—CO—, D-1-Tiq, D-3-Tiq, D-Atc, Aic, D-1-Piq, D-3-Piq or a L- or D-amino acid having a hydrophobic, basic or neutral side chain, which amino acid may optionally be N-(1–6C)alkyl substituted;

or A and B together are the residue $R^3R^4N$—$CHR^5$—C (O)—, wherein $R^3$ and $R^4$ independently are $R^1$, $R^1$—O—C(O)—, $R^1$—C(O)—, $R^1$—$SO_2$—, $R^2OOC$—$(CHR^2)_m$—$SO_2$—, $R^2OOC$—$(CHR^2)_m$—, $H_2NCO$—$(CHR^2)_m$—, or an N-protecting group, or one of $R^3$ and $R^4$ is connected with $R^5$ to form a 5- or 6-membered ring together with "N—C" to which they are bound, which ring may be fused with an aliphatic or aromatic 6-membered ring; and $R^5$ is a hydrophobic, basic or neutral side chain;

X is an L-amino acid with a hydrophobic side chain, serine, threonine, a cyclic amino acid optionally containing an additional heteroatom selected from N, O or S, and optionally substituted with (1–6C)alkyl, (1–6C) alkoxy, benzyloxy or oxo, or X is —$NR^2$—$CH_2$—C (O)— or the fragment

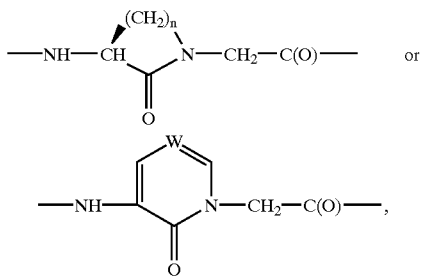

wherein n is 2, 3, or 4, and W is CH or N;
Y is H, —$CHF_2$, —$CF_3$, —CO—NH-(1–6C)alkylene-$C_6H_5$, —$COOR^6$ and $R^6$ being H or (1–6C)alkyl, —CONR⁷R⁸ and R⁷ and R⁸ being independently H or (1–6C)alkyl or R⁷ and R⁸ together being (3–6C) alkylene, or Y is a heterocycle selected from 2-thiazole, 2-thiazoline, 2-benzothiazole, 2-oxazole, 2-oxazoline and 2-benzoxazole, which heterocycles may optionally be substituted with (1–6C)alkyl, phenyl, (1–6C)alkoxy, benzyloxy or oxo;

and r is 0, 1, 2 or 3;

or a prodrug thereof or a pharmaceutically acceptable salt thereof, are potent and selective inhibitors. In addition, some of the compounds of the invention show good bioavailability after oral administration.

The compounds of the present invention are useful for treating and preventing thrombin-mediated and thrombin-associated diseases. This includes a number of thrombotic and prothrombotic states in which the coagulation cascade is activated which include, but are not limited to, deep vein thrombosis, pulmonary embolism, thrombophlebitis, arterial occlusion from thrombosis or embolism, arterial reocclusion during or after angioplasty or thrombolysis, restenosis following arterial injury or invasive cardiological procedures, postoperative venous thrombosis or embolism, acute or chronic atherosclerosis, stroke, myocardial infarction, cancer and metastasis, and neurodegenerative diseases. The compounds of the invention may also be used as anticoagulants in extracorporeal blood circuits, as necessary in dialysis and surgery. The compounds of the invention may also be used as in vitro anticoagulants.

DETAILED DESCRIPTION OF THE INVENTION

Preferred compounds according to the invention have the formula I, wherein X is an L-amino acid with a hydrophobic side chain, serine, threonine or —NR²—CH₂—C(O)—. Other preferred compounds of formula I are those, wherein A is as previously defined; B is a bond, an amino acid of the formula —NH—CH[(CH₂)ₚC(O)OH]—C(O)— or an ester derivative thereof with p being 0, 1, 2 or 3, —N((1–6C)alkyl)-CH₂—CO—, —N((2–6C)alkenyl)-CH₂—CO—, —N(benzyl)-CH₂—CO—, D-1-Tiq, D-3-Tiq, D-Atc, Aic, D-1-Piq, D-3-Piq or a D-amino acid having a hydrophobic side chain, which amino acid may optionally be N-(1–6C)alkyl substituted; or A and B together are the residue R³R⁴N—CH⁵—C(O)—; and X is a cyclic amino acid optionally containing an additional heteroatom selected from N, O or S, and optionally substituted with (1–6C)alkyl, (1–6C)alkoxy, benzyloxy or oxo, or X is —NR²—CH₂—C(O)— or the fragment

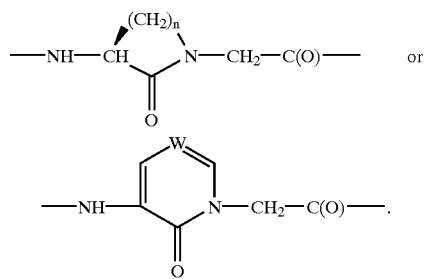

More preferred are compounds of formula I, wherein A is H, 2-hydroxy-3-cyclohexyl-propionyl-, 9-hydroxy-fluorene-9-carboxyl, R¹, R¹—SO₂—, R²OOC—(CHR²)ₘ—SO₂—, R²OOC—(CHR²)ₘ—, H₂NCO—(CH²)ₘ—, or an N-protecting group, wherein R¹ is selected from (1–12C)alkyl, (2–12C)alkenyl, (6–14C)aryl, (7–15C)aralkyl and (8–16C)aralkenyl; each group R² is independently H or has the same meaning as R¹; B is a bond, D-1-Tiq, D-3-Tiq, D-Atc, Aic, D-1-Piq, D-3-Piq or a D-amino acid having a hydrophobic side chain, which amino acid may optionally be N-(1–6C)alkyl substituted; or A and B together are the residue R³R⁴N—CHR⁵—C(O)—; Y is —CO—NH-(1–6C)alkylene-C₆H₅, —COOR⁶, —CONR⁷R⁸, or Y is a heterocycle selected from 2-thiazole, 2-thiazoline, 2-benzothiazole, 2-oxazole, 2-oxazoline and 2-benzoxazole. In particular preferred are those compounds, wherein A is H, R¹—SO₂— or R²OOC—(CHR²)ₘ—; B is a bond, D-1-Tiq, D-3-Tiq, D-Atc, Aic, D-1-Piq, D-3-Piq or a D-amino acid having a hydrophobic side chain; or A and B together are the residue R³R⁴N—CHR⁵—C(O)—, wherein at least one of R³ and R⁴ is R²OOC—(CHR²)ₘ— or R¹—SO₂— and the other independently is (1–12C)alkyl, (2–12C)alkenyl, (2–12C)alkynyl, (3–8C)cycloalkyl, (7–15C)aralkyl, R¹—SO₂— or R²OOC—(CHR²)ₘ—, and R⁵ is a hydrophobic side chain; Y is —CO—NH-(1–6C)alkylene-C₆H₅, —COOR⁶ and R⁶ being H or (1–3C)alkyl, —CONR⁷R⁸, R⁷ and R⁸ being independently H or (1–3C)alkyl or R⁷ and R⁸ together being (3–5C)alkylene, or Y is a heterocycle selected from 2-thiazole, 2-benzothiazole, 2-oxazole or 2-benzoxazole.

When A is R²OOC—(CHR²)ₘ—, preferably B is a D-amino acid having a hydrophobic side chain; or A and B together are the residue R³R⁴N—CHR⁵—C(O)—, wherein at least one of R³ and R⁴ is R²OOC—(CHR²)ₘ— and the other independently is (1–12C)alkyl, (2–6C)alkenyl, (3–8C)cycloalkyl, benzyl, R¹—SO₂— or R²OOC—(CHR²)ₘ—; and X is 2-azetidine carboxylic acid, proline, pipecolic acid, 4-thiazolidine carboxylic acid, 3,4-dehydro-proline, 2-octahydroindole carboxylic acid or —[N(3–8C)cycloalkyl]-CH₂—C(O)—. Most preferred are compounds wherein A is HOOC—CH₂—; B is D-Phe, D-Cha, D-Coa, D-Dpa, p-Cl-D-Phe, p-OMethyl-D-Phe, p-OEthyl-D-Phe, D-Nle, m-Cl-D-Phe, 3,4-di-OMe-D-Phe, or D-Chg; or A and B together are the residue R³R⁴N—CH⁵—C(O)—, wherein at least one of R³ and R⁴ is HOOC—CH₂— and the other independently is (1–4C)alkyl, (1–4C)alkyl-SO₂— or HOOC—CH₂— and R⁵ is (3–8C)cycloalkyl, (3–8C)cycloalkyl(1–4C)alkyl, phenyl, benzyl, optionally substituted with chlorine or (1–4C)alkoxy. Particularly preferred are those compounds wherein Y is a heterocycle selected from 2-thiazole, 2-benzothiazole, 2-oxazole or 2-benzoxazole.

When A is R¹—SO₂—, preferably B is a bond, D-1-Tiq, D-3-Tiq, D-Atc, Aic, D-1-Piq, D-3-Piq or a D-amino acid having a hydrophobic side chain; or A and B together are the residue R³R⁴N—CHR⁵—C(O)—, wherein at least one of R³ and R⁴ is R¹—SO₂— and the other independently is (1–12C)alkyl or R¹—SO₂—; X is 2-azetidine carboxylic acid, proline, pipecolic acid, 4-thiazolidine carboxylic acid, 3,4-dehydro-proline, 2-octahydroindole carboxylic acid, —[N(cyclopentyl)]-CH₂—C(O)— or the fragment

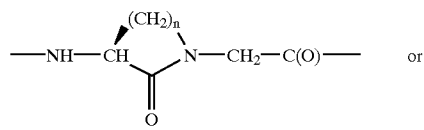

-continued

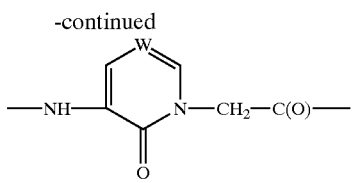

More preferred are those compounds wherein A is Ethyl-SO$_2$— or Benzyl-SO$_2$—; B is a bond, D-Phe, D-Cha, D-Coa, D-Dpa, p-Cl-D-Phe, p-OMethyl-D-Phe, p-OEthyl-D-Phe, D-Nle, m-Cl-D-Phe, 3,4-di-OMe-D-Phe, or D-Chg; or A and B together are the residue R$^3$R$^4$N—CHR$^5$—C(O)—, wherein at least one of R$^3$ and R$^4$ is Ethyl-SO$_2$— or Benzyl-SO$_2$— and the other independently is (1–12C)alkyl or R$^1$—SO$_2$— and R$^5$ is (3–8C)cycloalkyl, (3–8C)cycloalkyl(1–4C)alkyl, phenyl, benzyl, diphenylmethinyl, which groups are optionally substituted with chlorine or (1–4C)alkoxy. Most preferred are those compounds wherein Y is —CO—NH—CH$_2$—C$_6$H$_5$, —CO—NH—CH$_2$CH$_2$—C$_6$H$_5$ or —CONR$^7$R$^8$, R$^7$ and R$^8$ being independently H or (1–3C)alkyl or R$^7$ and R$^8$ together being (3–5C)alkylene, or Y is a heterocycle selected from 2-thiazole, 2-benzothiazole, 2-oxazole or 2-benzoxazole. Most preferably r is 1 in the compounds of formula I.

The N-protecting group as defined in the definition of moiety A is any N-protecting group as used in peptides. Suitable N-protecting groups can be found in T. W. Green and P. G. M. Wuts: Protective Groups in Organic Synthesis, Second Edition (Wiley, NY, 1991) and in The Peptides, Analysis, Synthesis, Biology, Vol. 3 E. Gross and J. Meienhofer, Eds., (Academic Press, New York, 1981).

The term optionally substituted D,L α-hydroxyacetyl means a group of the formula HO—CR$^a$R$^b$—C(O)—, wherein R$^a$ and R$^b$ independently are H, a hydrophobic side chain, or R$^a$ and R$^b$ together form a 5- or 6-membered ring, which is optionally fused with one or two aliphatic or aromatic 6-membered rings, and which 5- or 6-membered ring consists of carbon atoms and optionally one heteroatom selected from N, O and S. Preferred D,L α-hydroxyacetyl groups are 2-hydroxy-3-cyclohexyl-propionyl- and 9-hydroxy-fluorene-9-carboxyl.

The term (1–12C)alkyl means a branched or unbranched alkyl group having 1 to 12 carbon atoms, such as methyl, ethyl, t-butyl, isopentyl, heptyl, dodecyl, and the like. Preferred alkyl groups are (1–6C)alkyl groups, having 1–6 carbon atoms. More preferred are (1–4C)alkyl groups. Most preferred in the definition of R$^6$, R$^7$ and R$^8$ are (1–3C)alkyl groups, having 1–3 carbon atoms, such as methyl, ethyl, isopropyl.

A (2–12C)alkenyl group is a branched or unbranched unsaturated hydrocarbon group having 2 to 12 carbon atoms. Preferred are (2–6C)alkenyl groups. Examples are ethenyl, propenyl, allyl, and the like.

The term (1–6C)alkylene means a branched or unbranched alkylene group having 1 to 6 carbon atoms, such as —(CH$_2$)$_m$— and m is 1 to 6, —CH(CH$_3$)—, —CH(CH$_3$)—(CH$_2$)—, etc. Preferred alkylene groups in the definition of Y are ethylene and methylene.

A (2–12C)alkynyl group is a branched or unbranched hydrocarbon group containing a triple bond and having 2 to 12 carbon atoms. Preferred are (2–6C)alkynyl groups, such as ethynyl and propynyl.

A (6–14C)aryl group is an aromatic moiety of 6 to 14 carbon atoms. The aryl group may further contain one or more hetero atoms, such as N, S, or O. Examples of aryl groups are phenyl, naphthyl, (iso)quinolyl, indanyl, and the like. Most preferred is the phenyl group.

(7–15C)Aralkyl and (8–16C)aralkenyl groups are alkyl and alkenyl groups respectively, substituted by one or more aryl groups, the total number of carbon atoms being 7 to 15 and 8 to 16, respectively.

The term (1–6C)alkoxy means an alkoxy group having 1–6 carbon atoms, the alkyl moiety of which having the meaning as previously defined.

The term (3–8C)cycloalkyl means a cycloalkyl group having 3–8 carbon atoms, being cyclopropyl, cyclobutyl, cyclopentyl, cyclohexyl, cycloheptyl or cyclo-octyl. Cyclopentyl and cyclohexyl are preferred cycloalkyl groups.

The term halogen means fluorine, chlorine, bromine or iodine.

The term ester derivative means any appropriate ester derivative, preferably (1–4C)alkyl-esters, such as methyl-, ethyl- or t-butyl-esters.

The terms 1- and 3-Tiq mean 1,2,3,4-tetrahydroisoquinoline-1- or -3-carboxylic acid, respectively; 1- and 3-Piq are 1- and 3-carboxyperhydroisoquinoline, respectively; Atc is 2-aminotetralin-2-carboxylic acid; Aic is amino indane carboxylic acid; Phe is phenylalanine; Cha is cyclohexylalanine; Dpa is diphenylalanine; Coa is cyclooctylalanine; Chg is cyclohexylglycine; Nle is norleucine; Asp is aspartic acid.

The term hydrophobic side chain means a (1–12C)alkyl, optionally substituted with one or more (3–8C)cycloalkyl groups or (6–14C)aryl groups (which may contain a heteroatom, e.g. nitrogen) such as cyclohexyl, cyclo-octyl, phenyl, pyridinyl, naphthyl, tetrahydronaphthyl, and the like, which hydrophobic side chain may optionally be substituted with substituents such as halogen, trifluoromethyl, lower alkyl (for instance methyl or ethyl), lower alkoxy (for instance methoxy), phenyloxy, benzyloxy, and the like.

In the definitions, the term substituted means: substituted by one or more substituents. Amino acids having a basic side chain are for example, but not limited to, arginine and lysine, preferably arginine. The term amino acids having a neutral side chain refers to amino acids such as methionine sulphon and the like.

Cyclic amino acids are for example 2-azetidine carboxylic acid, proline, pipecolic acid, 1-amino-1-carboxy-(3–8C)cycloalkane (preferably 4C, 5C or 6C), 4-piperidine carboxylic acid, 4-thiazolidine carboxylic acid, 3,4-dehydroproline, azaproline, 2-octahydroindole carboxylic acid, and the like. Preferred are 2-azetidine carboxylic acid, proline, pipecolic acid, 4-thiazolidine carboxylic acid, 3,4-dehydroproline and 2-octahydroindole carboxylic acid. The term prodrug means a compound in which the alkynylamino side chain of the compound of formula I is protected, e.g. by a hydroxy, (1–6C)alkoxy or (1–6C)alkoxycarbonyl group.

The invention further includes a process for preparing a compound of formula I, including coupling of suitably protected amino acids or amino acid analogs, followed by removing the protective groups.

The compounds according to formula I may be prepared in a manner conventional for such compounds. The modified amino acid having an alkynylamino side chain is introduced in a way similar to methods known for other amino acids.

To that end, suitably Nα protected (and side-chain protected if reactive side-chains are present) amino acid derivatives or peptides are activated and coupled to suitably carboxyl protected amino acid or peptide derivatives either in solution or on a solid support. Protection of the α-amino functions generally takes place by urethane functions such as the acid-labile tert-butyloxycarbonyl group (Boc), benzyloxycarbonyl (Z) group and substituted analogs or the base-labile 9-fluorenyl-methyloxycarbonyl (Fmoc) group. The Z group can also be removed by catalytic hydrogenation. Other suitable amino protective groups include Nps, Bmv, Bpoc, Msc, etc. A good overview of amino protective groups is given is given in The Peptides, Analysis, Synthesis, Biology, Vol. 3 E. Gross and J. Meienhofer, Eds., (Academic Press, New York, 1981). Protection of carboxyl groups can take place by ester formation e.g. base-labile esters like methyl- or ethylesters, acid labile esters like tert-butylesters, or hydrogenolytically-labile esters like benzylesters. Protection of the alkynylamino side chain may be accomplished by using the aforementioned groups. Activation of the carboxyl group of the suitably protected amino acids or peptides can take place by the azide, mixed anhydride, active ester, or carbodiimide method, especially with the addition of catalytic and racemization-suppressing compounds like 1-hydroxybenzotriazole, N-hydroxysuccinimide, 3-hydroxy-4-oxo-3,4-dihydro-1,2, 3-benzotriazine, N-hydroxy-5-norbornene-2,3-dicarboximide. See, e.g. The Peptides, Analysis, Synthesis, Biology (see above) and Pure and Applied Chem. 59(3), 331–344 (1987).

The compounds of the invention, which can be in the form of a free base, may be isolated from the reaction mixture in the form of a pharmaceutically acceptable salt. The pharmaceutically acceptable salts may also be obtained by treating the free base of formula I with an organic or inorganic acid such as hydrogen chloride, hydrogen bromide, hydrogen iodide, sulfuric acid, phosphoric acid, acetic acid, propionic acid, glycolic acid, maleic acid, malonic acid, methanesulphonic acid, fumaric acid, succinic acid, tartaric acid, citric acid, benzoic acid, and ascorbic acid.

The compounds of this invention possess one or more chiral carbon atoms, and may therefore be obtained as a pure enantiomer, or as a mixture of enantiomers, or as a mixture containing diastereomers. Methods for obtaining the pure enantiomers are well known in the art, e.g. crystallization of salts which are obtained from optically active acids and the racemic mixture, or chromatography using chiral columns. For diastereomers straight phase or reversed phase columns may be used.

The compounds of the invention may be administered enterally or parenterally, and for humans preferably in a daily dosage of 0.001–100 mg per kg body weight, preferably 0.01–10 mg per kg body weight. Mixed with pharmaceutically suitable auxiliaries, e.g. as described in the standard reference, Gennaro et al., Remington's Pharmaceutical Sciences, (18th ed., Mack Publishing Company, 1990, see especially Part 8: Pharmaceutical Preparations and Their Manufacture) the compounds may be compressed into solid dosage units, such as pills, tablets, or be processed into capsules or suppositories. By means of pharmaceutically suitable liquids the compounds can also be applied in the form of a solution, suspension, emulsion, e.g. for use as an injection preparation, or as a spray, e.g. for use as a nasal spray.

For making dosage units, e.g. tablets, the use of conventional additives such as fillers, colorants, polymeric binders and the like is contemplated. In general any pharmaceutically acceptable additive which does not interfere with the function of the active compounds can be used. Suitable carriers with which the compositions can be administered include lactose, starch, cellulose derivatives and the like, or mixtures thereof, used in suitable amounts.

The invention is further illustrated by the following examples.

EXAMPLES

The terms -LysininylΨ[COCO]—OH, -Lysininyl-OMe and -Lysininyl-(2-thiazolyl) mean a residue of the following formula:

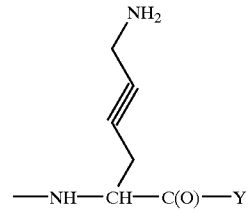

wherein
Y=COOH, OCH$_3$ and 2-thiazolyl, respectively.
Azt=2-azetidine carboxylic acid; Boc=tert-butyloxycarbonyl; Cbz=benzyloxycarbonyl; Bzl=benzyl.

Example 1

HOOC—CH$_2$-D-Cha-Pro-Lysininyl-(2-thiazolyl)
(a). 1-Amino-4-chloro-2-butyne hydrochloride 1,4-Dichloro-2-butyne (73.8 g) was dissolved in chloroform (600 ml). Hexamine (84.0 g) was added and the reaction mixture was heated under reflux for 2.5 h and then cooled for 24 h at 5° C. The hexamine complex was filtered off (220 g). A solution of the complex in ethanol (1l) was stirred for 24 h at room temperature with concentrated hydrochloric acid (180 ml). The precipitated ammonium chloride was filtered off and the filtrate was concentrated under reduced pressure until crystallization was incipient. Addition of diethylether then precipitated the hydrochloride of 1-amino-4-chloro-2-butyne. Recrystallization from ethanol/ether afforded 1-amino-4-chloro-2-butyne hydrochloride (59.75 g).

TLC: R$_f$=0.60, silica gel, dichloromethane/methanol/water 70/30/5 v/v/v.
(b). 1-Acetylamino4-chloro-2-butyne 1-Amino-4-chloro-2-butyne hydrochloride (59.75 g) was dissolved in 10% aqueous sodium acetate-solution (335 ml). Ethyl acetate (500 ml) was added, and acetic anhydride (70 ml) was added dropwise at room temperature. A 25% aqueous sodium acetate solution was added to pH 5 and the solution was stirred for 30 min at room temperature. The ethyl acetate layer was separated, and the aqueous layer was extracted twice with ethyl acetate. The combined organic layers were washed with water, brine and dried over sodium sulphate, filtered and evaporated in vacuo yielding 1-acetylamino4-chloro-2-butyne as a yellow syrup (58.8 g).

TLC: R$_f$=0.99, silica gel, dichloromethane/methanol/water 70/30/5 v/v/v.
(c). Acetamido(4-acetamido-2-butynyl)-malonic acid diethyl ester To a cold (0° C.) solution of sodium hydride (60% dispersion in mineral oil, 3.48 g) in dioxane (70 ml) was added dropwise absolute ethanol (70 ml). The mixture was allowed to warm to room temperature and a solution of diethyl acetamido malonate (20.5 g) in dioxane (70 ml) was added dropwise. Sodium iodide (9.07 g) was added and a solution of 1-acetylamino-4-chloro-2-butyne (11 g) in dioxane (140 ml) was added dropwise at room temperature. After addition of another 100 ml of ethanol the mixture was refluxed for 2.5 h. The reaction mixture was cooled and the precipitate formed was filtered off. Purification using chromatography on silica (eluent: ethyl acetate/methanol 9/1 v/v) yielded acetamido(4-acetamido-2-butynyl)-malonic acid diethyl ester. (15.9 g).

TLC: $R_f$=0.25, silica gel, ethyl acetate.

(d). 2,6-Diamino-4-hexynoic acid dihydrochloride (H-Lysinine dihydrochloride)

Acetamido(4-acetamido-2-butynyl)-malonic acid diethyl ester (7.64 g) was dissolved in a mixture of acetic acid (140 ml) and a 6M hydrochloric acid solution (290 ml), and heated overnight at 95° C. The mixture was concentrated in vacuo. The residue was crystallized from ethanol/water yielding 2,6-diamino-4-hexynoic acid dihydrochloride as a crystalline powder (4.0 g).

(e). Boc-Lysininyl(Cbz)-OH

Copper(II)sulphate pentahydrate (287 mg) was added to a solution of 2,6diamino-4-hexynoic acid dihydrochloride (500 mg) in 17 ml dioxane/water 3/2 v/v and the pH was adjusted to 9 by adding a 2 M sodium hydroxide solution. N-(benzyloxycarbonyloxy)-succinimid (573 mg) in dioxane (10 ml) was added dropwise at room temperature along with a 2 M sodium hydroxide solution to keep the pH around 9–9.5. After the addition was complete, the reaction mixture was stirred overnight at room temperature. The mixture was filtered and the thus obtained precipitate was suspended in dioxane (20 ml). Di-tert-butyl dicarbonate (500 mg) was added and the pH was adjusted to 12–13 by adding a 4 M sodium hydroxide-solution. The reaction mixture was stirred overnight at room temperature. The mixture was filtered and the filtrate was diluted with water. A 4M hydrochloric acid solution was added until pH 2 and the waterlayer was extracted twice with dichloromethane. The combined organic phases were washed with water and dried over sodium sulphate and the solvent was removed by evaporation yielding Boc-Lysininyl(Cbz)-OH (540 mg).

TLC: $R_f$=0.70, silica gel, ethyl acetate/pyridine/acetic acid/water 63/20/611 11 v/v/v/v.

(f). Boc-Lysininyl(Cbz)-NMeOMe

N,O-dimethyl-hydroxylamine hydrochloride (363 mg) and [2-(1H-benzotriazol-1-yl)-1,1,3,3-tetramethyluronium tetrafluoroborate] (1.2 g) were added to a solution of Boc-Lysininyl(Cbz)-OH (1.4 g) in dichloromethane (50 ml) and the pH was adjusted to pH 9–10 by adding N,N-diisopropylethylamine. The reaction mixture was stirred for 1 h at room temperature. The mixture was washed successively with a cold 2 M hydrochloric acid solution, water, 5% aqueous sodium hydrogencarbonate solution and water. The organic layer was dried over sodium sulphate, filtered and evaporated. The residue was purified by chromatography on silica (eluent: ethyl acetate/heptane 3/2 v/v) to yield Boc-Lysininyl(Cbz)-NMeOMe (1.37 g).

TLC: $R_f$=0.70, silica gel, ethyl acetate/heptane 4/1 v/v.

(g). Boc-Lysininyl(Cbz)-(2-thiazolyl)

A solution of 2-bromothiazole (1.78 g) in diethylether (10 ml) was added dropwise to a cold (−78° C.) stirred solution of n-butyl lithium (10.9 mmol) in diethylether (10.9 ml). After the solution had been stirred at −78° C. for 30 min, a solution of Boc-Lysininyl(Cbz)-NMeOMe (1.37 g) in dry tetrahydrofuran (15 ml) was added slowly. The mixture was stirred at −78° C. for 1 h, then 5% aqueous sodium hydrogen carbonate solution was added. The mixture was allowed to warm to room temperature and the layers were separated. The aqueous layer was extracted with diethylether. The combined organic layers were washed with water, dried over sodium sulphate and evaporated. The residue was purified by chromatography on silica (eluent: ethyl acetate/heptane 1/1 v/v) to yield Boc-Lysininyl(Cbz)-(2-thiazolyl) (1.21 g).

TLC: $R_f$=0.72, silica gel, ethyl acetate/heptane 3/1 v/v.

(h). H-L sininyl(Cbz)-(2-thiazolyl).TFA

Boc-Lysininyl(Cbz)-(2-thiazolyl) (1.21 g) was dissolved in trifluoroacetic acid (TFA)/dichloromethane (15 ml; 1/1 v/v) and stirred for 1 h at room temperature. The crude amine was isolated as a yellow oil in quantitative yield after removal of the solvent by evaporation, and used immediately to prepare N-Boc-N-(tert-butyloxycarbonylmethyl-D-Cha-Pro-Lysininyl(Cbz)-(2-thiazolyl).

TLC: $R_f$=0.25, silica gel, ethyl acetate/pyridine/acetic acid/water 63/20/6/11 v/v/v/v.

(i). H-D-Cha-OMe.HCl

To cold (−20° C.) and dry methanol (195 ml) was added dropwise thionylchloride (28 ml). H-D-Cha-OH.HCl (40 g) was added and the reaction mixture was heated under reflux for 5 h. The mixture was concentrated in vacuo and coevaporated with methanol (3 times). The residue was crystallized from methanoldiethylether yielding H-D-Cha-OMe.HCl as a white crystalline powder (40.9 g), TLC: $R_f$=0.66, silica gel, n-butanol/acetic acid/water 10/1/3 v/v/v.

(j). N-(t-Butyloxycarbonylmethyl)-D-Cha-OMe t-Butyl-bromoacetate (36 g) was added to a stirred solution H-D-Cha-OMe.HCl (40.9 g) in 400 ml of acetonitrile. The pH of the mixture was adjusted to 8.5 with N,N-diisopropylethylamine. The mixture was stirred for 16 hours at room temperature and evaporated in vacuo. The residue was dissolved in dichloromethane and the solution was washed with water, dried on sodium sulphate and evaporated in vacuo. Chromatography over silica gel in heptane/ethyl acetate 9/1 (v/v) gave 64 g of N-(t-butyloxycarbonylmethyl)-D-Cha-OMe.

TLC: $R_f$=0.25, silica gel, ethyl acetateiheptane 1/1 v/v.

(k). N-t-Butyloxcarbonylmethyl)-N-Boc-D-Cha-OMe

The pH of a solution of N-(t-butyloxycarbonylmethyl)-D-Cha-OMe (64 g) and di-t-butyl dicarbonate (40.3 g) in N,N-dimethylformamide (500 ml) was adjusted to 8.5 with N,N-diisopropylethylamine. The mixture was stirred for 16 hours at room temperature. The solvent was removed in vacuo. Dichloromethane and water were added to the residue. The organic layer was separated, washed with cold 1N hydrochloric acid, water, 5% sodium hydrogen carbonate and water. The organic layer was dried on sodium sulphate and the filtrate was evaporated to an amorphous solid of N-(t-Butyloxycarbonylmethyl)-N-Boc-D-Cha-OMe with a yield of 59.6 g.

TLC: $R_f$=0.50, silica gel, ethyl acetate/heptane 1/1 v/v.

(l). N-(t-Butyloxycarbonylmethyl-N-Boc-D-Cha-OH

A solution of N-(t-Butyloxycarbonylmethyl)-N-Boc-D-Cha-OMe (59.6 g) in 900 ml of dioxane/water 9/1 (v/v) was treated with sufficient 6N sodium hydroxide to keep the pH at 12 for 6 hours at room temperature. After acidification, the mixture was poured into water and extracted with dichloromethane. The organic layer was washed with water and dried on sodium sulphate. The filtrate was evaporated and yielded 54 g of N-(t-Butyloxycarbonylmethyl)-N-Boc-D-Cha-OH.

TLC: $R_f$=0.60, silica gel, dichloromethane/methanol 9/1 v/v.

(m). N-(t-Butyloxycarbonylmethyl)-N-Boc-D-Cha-OSu

A solution of N-(t-Butyloxycarbonylmethyl)-N-Boc-D-Cha-OH (12.5 g) in 200 ml acetonitrile was treated with N-hydroxysuccinimide (4.1 g) and 1-(3-dimethylaminopropyl)-3-ethylcarbodiimide hydrochloride (6.84 g) overnight at room temperature. The reaction mixture was evaporated to dryness and the residue was dissolved in ethyl acetate. The organic phase was washed with water, dried over sodium sulphate and concentrated to afford the active ester, which was directly used in the next step.

(n). N-(t-Butyloxycarbonylmethyl)-N-Boc-D-Cha-Pro-OH

H-Pro-OH.HCl (7.5 g) was dissolved in 100 ml water. The pH of the reaction mixture was adjusted to 8 with a 1 N sodium hydroxide solution, whereafter N-(t-Butyloxycarbonylmethyl)-N-Boc-D-Cha-OSu, dissolved in 100 ml of N,N-dimethylformamide, was added dropwise. The reaction was stirred overnight at room temperature at pH≈8. The reaction mixture was cooled and adjusted to pH≈2 with 1N hydrochloric acid. The aqueous layer was extracted with ethyl acetate. The organic phase was washed with water, dried over sodium sulphate en evaporated in vacuo. Silica gel purification, using a gradient ethyl acetate/methanol 9/1→1/1 (v/v) afforded 11.0 g of the desired dipeptide.

TLC: $R_f$=0.81, silica gel, ethyl acetate/pyridine/acetic acid/water 163/20/6/11 v/v/v/v.

(o). N-Boc-N-(tert-butyloxycarbonylmethyl)-D-Cha-Pro-Lysininyl(Cbz)-(2-thiazolyl)

N-Boc-N-(tert-butyloxycarbonylmethyl)-D-Cha-Pro-OH (1.31 g) was dissolved in dry N,N-dimethylformamide (15 ml). After addition of triethylamine (750 µl), the reaction mixture was placed under nitrogen and cooled to −15° C. Isobutyl chloroformate (352 µl) was subsequently added and the mixture was allowed to stir for 15 min at −15° C. H-Lysininyl(Cbz)-(2-thiazolyl).TFA (1.15 g) was dissolved in dry N,N-dimethylformamide (10 ml) and added dropwise to the cold mixed anhydride solution, maintaining the pH at 8.5 by addition of triethylamine. The reaction mixture was stirred for 30 min at −15° C. The reaction mixture was evaporated to dryness. The residue was dissolved in ethyl acetate and successively washed with water, 5% aqueous sodium hydrogen carbonate solution, water and brine, dried over sodium sulphate and concentrated in vacuo. The residue was purified by chromatography on silica (eluent: dichloromethane/methanol 95/5 v/v) to yield N-Boc-N-(tert-butyloxycarbonylmethyl)-D-Cha-Pro-Lysininyl(Cbz)-(2-thiazolyl) (1.77 g).

(p). HOOC—CH$_2$-D-Cha-Pro-Lysininyl-(2-thiazolyl)

N-Boc-N-(tert-butyloxycarbonylmethyl)-D-Cha-Pro-Lysininyl(Cbz)-(2-thiazolyl) (1.77 g) was treated with trifluoroacetic acid/thioanisole 10/1 v/v (20 ml) for 4 h at room temperature. The reaction mixture was concentrated in vacuo and the residue was dissolved in water. The aqueous phase was washed extensively with diethylether. The water layer was charged directly onto a preparative HPLC Supelcosil LC-18-BD column using a gradient elution system of 20% A/70% B/10% C to 20% A/50% B/30% C over 45 min, at a flow rate of 20 ml/min. (A: 0.5M phosphate buffer pH 2.1, B: water, C: acetonitril/water 3/2 v/v).

Yield of two diastereomers:

300 mg. Massa: ESI$^+$: 518.5 [AH]$^+$; 259.8 [AH2]$^{2+}$
$R_t$(LC): 28.81 min; 20% A/80% B to 20% A/20% B/60% C in 40 min 500 mg. Massa: ESI$^+$: 518.5 [AH]$^+$; 259.8 [AH2]$^{2+}$
$R_t$(LC): 29.88 min; 20% A 80% B to 20% A/20% B/60% C in 40 min Example 2

N-Me-D-Phe-Pro-LysininylΨ[COCO]—OH (a). Boc-Lysininyl(Cbz)-OMe

[2-(1H-benzotriazol)-1,1,3,3-tetramethyluronium tetrafluoroborate] (1.83 g) was added to a solution of Boc-Lysininyl(Cbz)-OH (2.15 g) in a mixture of dichloromethane:methanol 9:1 (25 ml) and the pH was adjusted to 7–8 by adding N,N-diisopropylethylamine. The reaction mixture was stirred for 1 h at room temperature. The mixture was washed with 1 N hydrochloric acid. water, 5% sodium hydrogen carbonate solution and water. The organic layer was dried over anhydrous sodium sulphate, filtered and concentrated in vacuo. The residue was purified by chromatography on silica in ethyl acetate/heptane 6/4 v/v Yield 2.17 g.

Rf=0.5, silicagel, in ethyl acetate:heptane 3/1 v/v.

(b). 2-Acetoxy-3-(t-butyloxycarbonylamino)-7-(benzyloxycarbonylamino)-hept-5-yn-nitrile At −78° C., to a stirred solution of 2 g of Boc-Lysininyl-OMe in 60 ml of dichloromethane was added 18.2 ml of a precooled solution of diisobutylaluminium hydride (1.0 M solution in hexane) at such a rate to keep the temperature below −70° C. The solution was stirred for ½ h. The mixture was poured into a solution of citric acid in water and extracted with dichloromethane. The combined extracts were washed with water, 5% sodium hydrogen carbonate solution and water, dried on anhydrous sodium sulphate and filtered. The filtrate was concentrated in vacuo to yield 2.25 g of an oil. The crude product was dissolved in 25 ml of dichloromethane. The solution was cooled to 0° C., and 0.31 g of benzyl triethyl ammonium chloride, 1.2 ml of acetic anhydride and a solution of 2.5 g of sodium cyanide in 75 ml of water were added. The mixture was stirred vigorously for 30 min at 0–5° C. The organic layer was separated, washed twice with water, dried on anhydrous sodium sulphate and evaporated to dryness. The residue was chromatographed on silica in heptane:ethyl acetate 8:2 (v/v) and gave 1.4 g of 2-acetoxy-3-(t-butyloxycarbonylamino)-7-(benzyloxycarbonylamino)-hept-5-yn-nitrile.

Rf=0.6, silicagel, in heptane:ethyl acetate 1/1 v/v.

(c). H-Lysininyl(Cbz)Ψ[CHOHCO]—OH

At −20° C., 6.5 g of gaseous hydrogen chloride were led into a solution of 1.4 g of 2-acetoxy-3-(butyloxycarbonylamino)-7-(benzyloxycarbonylamino)-hept-5-yn-nitrile in a mixture of diethyl ether/methanol 9/1 v/v. The mixture was stirred overnight at 0–4° C. The mixture was then cooled to −20° C., and 6.75 ml of water was added. The reaction mixture was stirred for 4 h at 20° C. The organic layer was separated. The pH of the aqueous phase was adjusted to 10 with 1 N sodium hydroxide, followed by extraction with 1-butanol. The combined extracts were washed with brine and concentrated in vacuo and gave 650 mg of H-Lysininyl(Cbz)Ψ[CHOHCO]—OH.

Rf=0.17 in ethyl acetate/pyridineacetic acid/water 63/20/6/11 v/v/v/v.

(d). N-Boc-N-Me-D-Phe-OH

Commercially available H-N-Me-D-Phe-OH (11 g) was dissolved in a mixture of dioxane/water 1/2 (165 ml) followed by the addition of di-tert-butyl dicarbonate (19.1 g). The pH of the reaction mixture was kept at 8.5–9 using sodium hydroxide as base. Next, the reaction mixture was concentrated in vacuo and the residue was dissolved in ethyl acetate. The organic phase was washed with 0.1 N hydrochloric acid and saturated sodium chloride, dried over sodium sulphate, filtered and evaporated to dryness to give 17.1 g product.

TLC: Rf=0.35, silica gel, dichloromethane/methanol 8/2 v/v.

(e). N-Boc-N-Me-D-Phe-Pro-OH

N-Boc-N-Me-D-Phe-OH (17.1 g) and H-Pro-OMe.HCl (10.1 g) were coupled according to the procedures as described for the synthesis of N-(t- butyloxycarbonylmethyl)-N-Boc-D-Cha-Pro-OBzl (see example 1). The obtained dipeptide, N-Boc-N-Me-D-Phe-Pro-OMe (22.6 g), was dissolved in dioxane/water 9/1 (200 ml) and treated with 4 N sodium hydroxide (21.7 ml) at room temperature overnight. The reaction mixture was diluted with 300 ml ice water, acidified (pH 2) using 4 N hydrochloric acid and extracted with dichloromethane. The combined organic layers were washed with saturated sodium chloride, dried over sodium sulphate, filtered and evaporated to dryness to give the crude product. Crystallisation from diethylether/heptane 2/3 v/v afforded pure N-Boc-N-Me-D-Phe-Pro-OH (12.6 g).

TLC:Rf=0.20, silica gel, toluene/ethyl acetate 6/4 v/v.

(f). N-Boc-N-Me-D-Phe-Pro-Lysininyl(Cbz)Ψ[CHOHCO]—OH

Isobutyl chloroformate (0.101 g) was added to a solution of N-Boc-N-Me-D-Phe-Pro-OH (0,195 g) in N,N-dimethylformamide (10 ml) at −20° C., and the pH of the mixture was adjusted to 8 with triethylamine. A solution of H-Lysininyl(Cbz)Ψ[CHOHCO]—OH (0.3 g) in N,N-dimethylformamide (10 ml) of which the pH was adjusted to 8.5 with triethylamine, was added to the reaction mixture at −20° C. The mixture was stirred overnight. The reaction was incomplete, therefore a solution of N-Boc-N-Me-D-Phe-Pro-OH (293 mg) in N,N-dimethylformamide (5 ml) was treated at 0° C. with N-hydroxysuccinimide (95 mg) and 1,3-dicyclohexylcarbodiimide at pH 8.5 and was added to the reaction mixture. The mixture was stirred for 4 h at room temperature. The volatiles were removed in vacuo. The residue was dissolved in dichloromethane. The solution was washed with water, dried on sodium sulphate and evaporated to dryness. The residue was chromatographed over silica gel in ethyl acetate/pyridine/acetic acid/water 63/5/1.5/2.75 v/v/v/v.

The fractions were pooled and gave 0.26 g of N-Doc-N-Me-D-Phe-Pro-Lysininyl(Cbz)Ψ[CHOHCO]—OH.

Rf=0.24 in ethyl acetate/pyridine/acetic acid/water 63/5/1.5/2.75 v/v/v/v.on silica.

(g). N-Boc-N-Me-D-Phe-Pro-Lysininyl(Cbz)Ψ[COCO]—OH

A solution of N-Boc-N-Me-D-Phe-Pro-Lysininyl(Cbz)Ψ[CHOHCO]—OH (260 mg) in 20 ml of dichloromethane was treated with 1,1,1-triacetoxy-1,1-dihydro-1,2-benziodoxol-3 (1H)-one (180 mg). The mixture was stirred for 3½ h at room temperature, washed with a sodium thiosulphate solution and water. The organic layer was dried on anhydrous sodium sulphate and evaporated to dryness and gave 0.35 g of N-Boc-N-Me-D-Phe-Pro-Lysininyl(Cbz)Ψ[COCO]—OH together with some degradation products of the reagent.

Rf=0.36 in ethyl acetate/pyridine/acetic acid/water 63/20/6/11 v/v/v/v on silica.

(h). N-Me-D-Phe-Pro-LysininylΨ[COCO]—OH

A solution of N-Boc-N-Me-D-Phe-Pro-Lysininyl(Cbz)Ψ[COCO]—OH (0.3 g) in a mixture of trifluoroacetic acid/thioanisole 10/1 v/v (10 ml) was stirred for 4 h at room temperature. The reaction mixture was concentrated in vacuo, dissolved in water and washed diethylether. The residue was dried in vacuo and gave 430 mg of crude N-Me-D-Phe-Pro-LysininylΨ[COCO]—OH, which was purified on a preparative HPLC Supelcosil LC-18-DB column using a gradient elution system of A 20%; B 80%; C 0% to A 20%; B 70%; C 10%, over 45 min and at a flow rate of 20 ml/min.

Yield of two diasteromers:
53.7 mg; MS: FAB$^+$ 429.1 [M+H]; FAB$^-$ 426.9 [M−H] Rt (LC): 15.25 min; A: 20%; B: 80%; C: 0% to A: 20%; B: 20%; C: 60% in 40 min.

51.6 mg; MS: FAB$^+$ 429.1 [M+H]; FAB$^-$ 426.8 [M−H] Rt (LC: 16.30 min; A: 20%; B: 80%; C: 0% to A: 20%; B: 20% C: 60% in 40 min.

Example 3

N-Me-D-Cha-Pro-LysininylΨ[COCO]—OH (a). N-Me-N-Boc-D-Cha-Pro-OH

N-Me-N-Boc-D-Cha-Pro-OH was prepared according to the same procedures as described in example 2(e), starting from N-Me-N-Boc-D-Cha-OH and H-Pro-OMe.HCl.

TLC: Rf=0.26, silica gel, ethyl acetate/methanol 4/1 v/v.

(b). Boc-Lysininyl(Cbz)Ψ[CHOHCO]—OMe.

A solution of 2-Acetoxy-3-(t-butyloxycarbonylamino)-7-(benzyloxycarbonylamino)-hept-5-yn-nitrile (36 g) in diethylether/methanol 3/1 v/v (1l) was cooled to −20° C. Gaseous hydrogen chloride was passed through the solution until a concentration of 3 M (109 g) was reached, whereafter the mixture was stired overnight at 0–4° C. Water (170 ml) was added, in such a rate to keep the temperature <5° C. Next, the reaction mixture was allowed to warm up and stirred for another 5 hours at room temperature. The organic phase was separated. The pH of the water layer was adjusted to 10 with dilute sodium hydroxide, followed by the extraction with 1-butanol. The combined extracts were washed with brine, dried over sodium sulphate and evaporated to dryness to give H-Lysininyl(Cbz)Ψ[CHOHCO]—OMe (58 g). Di-tert-butyl dicarbonate (18.4 g) was added to a solution of H-Lysininyl(Cbz)Ψ[CHOHCO]—OMe (58 g) in methanol and the pH was adjusted to 8 by adding triethylamine. The reaction mixture was stirred at room temperture. After the reaction was complete, it was concentrated in vacuo. The residu was dissolved in ethyl acetate and washed with 0.1 N hydrochloric acid solution and brine. The organic layer was dried over magnesium sulphate, filtered and evaporated. The residu was purified by chromatography on silica (eluent: gradient of heptane/ethyl acetate 7/3 v/v, to ethyl acetate to ethyl acetate/methanol 8/2 v/v). The fractions were pooled and gave 4.76 g Boc-Lysininyl(Cbz)ψ[CHOHCO]—OMe.

TLC: $R_f$=0.40, silica gel, dichloromethane/methanol 9/1 v/v.

Furthermore a side product was isolated and characterised as Boc-Lysininyl(Cbz)Ψ[CHOHCO]—OBu (0.94 g).

TLC: $R_f$=0.47, silica gel, dichloromethane/methanol 9/1 v/v.

(c). H-Lysininyl(Cbz)Ψ[CHOHCO]—OMe. TFA

According to the method as described in example 1h, Boc-Lysininyl(Cbz)Ψ[CHOHCO]—OMe (500 mg) was converted into the title compound (500 mg) and immediately used in the coupling.

TLC: Rf=0.12, silica gel, dichloromethane/methanol 95/5 v/v .

(d). N-Me-N-Boc-D-Cha-Pro-Lysininyl(Cbz)Ψ[CHOHCO]—OMe

To a cold (0° C.) solution of N-Me-N-Boc-D-Cha-Pro-OH (546 mg) in N,N-dimethylformamide (10 ml) were succesively added 1-hydroxy benzotriazole (202 mg), dicyclohexyl carbodiimide (308 mg) and H-Lysininyl(Cbz)Ψ[CHOHCO]—OMe. TFA (516 mg) whereafter the pH of the solution was adjusted to 8 with triethylamine. The reaction mixture was stirred for 1 hour at 0° C. and then kept at room temperature overnight. The mixture was cooled to −20° C. and dicyclohexylurea was removed by filtration. The filtrate was evaporated to dryness. The residue was dissolved in ethyl acetate and washed succesively with 1 N hydrochloric acid, water, 5% sodium hydrogen carbonate and water, dried over sodium sulphate and concentrated in vacuo. The residue was chromatographed on silica gel in heptane/ethyl acetate 1/1→1/4 (v/v) as eluent. The fractions containing N-Me-N-Boc-D-Cha-Pro-Lysininyl(Cbz)Ψ[CHOHCO]-OMe were pooled and evaporated. Yield: 544 mg.

TLC: Rf=0.39, silica gel, dichloromethane/methanol 95/5 v/v.

(e). N-Me-N-Boc-D-Cha-Pro-Lysininyl(Cbz)Ψ[CHOHCO]—OH

N-Me-N-Boc-D-Cha-Pro-Lysininyl(Cbz)Ψ[CHOHCO]—OMe (544 mg) was dissolved in dioxane/water 7/3 (v/v) (13 ml) and treated with 2 N sodium hydroxide solution (0.61 ml) for 1 hour at room temperature. The reaction mixture was diluted with water (30 ml), 2 N hydrochloric acid solution was added until pH 2 and the water layer was extracted with dichloromethane. The combined organic phases were washed with water, brine and dried over sodium sulphate, filtered and concentrated in vacuo to afford the desired product. Yield: 560 mg.

TLC. Rf=0.47, silica gel, dichloromethane/methanol 4/1 v/v.

(f). N-Me-N-Boc-D-Cha-Pro-Lysininyl(Cbz)Ψ[COCO]—OH

N-Me-N-Boc-D-Cha-Pro-Lysininyl(Cbz)Ψ[CHOHCO]—OH (500 mg) was dissolved in 2.3 ml of a 0.5 M solution of 1-hydroxy-1,2-benziodoxol-3 (1H)-one 1-oxide in dimethyl sulfoxide and stirred overnight at room temperature. The reaction mixture was quenched with a solution of sodium thiosulphate (1.25 g) in 150 ml water, cooled with an ice bath whereafter the pH of the solution was adjusted to 2 with 2 N hydrochloric acid. The water layer was extracted with dichloromethane and the combined organic layers were washed with a saturated sodium chloride solution. The organic phase was dried over sodium sulphate, filtered and evaporated in vacuo to give crude N-Me-N-Boc-D-Cha-Pro-Lysininyl(Cbz)Ψ[COCO]—OH.

TLC: Rf=0.71, silica gel, ethyl acetate/pyridine/acetic acid/water 88/31/18/7 v/v/v/v.

(g). N-Me-D-Cha-Pro-Lysininyl Ψ[COCO]—OH

Crude N-Me-N-Boc-D-Cha-Pro-Lysininyl(Cbz)Ψ[COCO]—OH was treated under the same conditions as described in example 2 h to afford, after HPLC purification, 175 mg of pure N-Me-D-Cha-Pro-Lysininyl Ψ[COCO]—OH as a diastereomeric mixture.

Rt (LC): 22.19 and 22.83 min, 20% A, 80% B to 20% A, 20% B and 60% C in 40 min.

Example 4

3,3-Diphenylpropionyl-Pro-Lysininyl Ψ[COCO]—OH (a). 3.3-Diphenylpropionyl-prolyl-OH 3,3-Diphenylpropionyl-prolyl-OH (5.2 g) was prepared, according to the same procedures as described in example 2e, using 3,3-diphenylpropionic acid (5.0 g) and H-Pro-OMe.HCl (3.66 g).

TLC: $R_f$=0.65, silica gel, ethyl acetate/pyridine/acetic acid/water 63/20/6/11 v/v/v/v (b). 3,3-Diphenylpropionyl-Pro-Lysininyl(Cbz)Ψ[CHOHCO]—OMe According to the same procedures as described in example 3,3,3-diphenylpropionyl-prolyl-OH (648 mg) was coupled with H-Lysininyl(Cbz)Ψ[CHOHCO]—OMe. TFA (722 mg) to afford the protected tripeptide 3,3-diphenylpropionyl-Pro-Lysininyl(Cbz)Ψ[CHOHCO]—OMe (1.13 g), after purification.

TLC: Rf=0.40, silica gel,dichloromethane/methanol 95/5 v/v.

(c). 33-Diphenylpropionyl-Pro-Lysininyl Ψ[COCO]—OH 3,3-Diphenylpropionyl-Pro-Lysininyl(Cbz)Ψ[CHOHCO]—OMe (860 mg) was saponified according to the same procedure as described in example 3(e). The crude product was oxidized in dichloromethane (80 ml) using 1,1,1-triacetoxy-1,1-dihydro-1,2benziodoxol-3 (1H)-one (594 mg) as described in example 2g. Subsequent deprotection in TFA and thioanisole (example 2h) gave 3,3-Diphenylpropionyl-Pro-Lysininyl Ψ[COCO]—OH (229 mg) as a diastereomeric mixture.

Rt (LC): 20.31 min, 20% A, 60% B and 20% C to 20% A, 80% C in 30 min.

Example 5

BenzylSO$_2$-norLeu(cyclo)-Gly-Lysininyl Ψ[COCO]—OH norLeu(cyclo)-Gly means a structural fragment of the formula

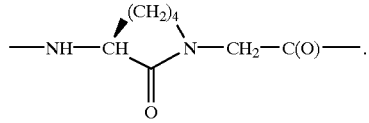

(a). N-Boc-L-α-Amino-ε-caprolactam

To a stirred solution of (10 g) in dioxane/water (2/1 v/v) (30 ml) was added 1 N sodium hydroxide solution (7.8 ml) followed by di-t-butyl dicarbonate (18.8 g). The mixture was stirred for 16 h. at room temperature and concentrated in vacuo. The residue was dissolved in ethyl acetate and washed with water and brine, dried over sodium sulphate, filtered and evaporated in vacuo. The crude material was triturated by hexane, filtered and dried in vacuo to yield N-Boc-L-α-Amino-ε-caprolactam (16 g).

TLC: Rf=0.85, silica gel, ethyl acetate/heptane 1/1 v/v.

(b). Boc-norLeu(cyclo)-Gly-OMe

N-Boc-L-α-Amino-ε-caprolactam (10 g) was dissolved in dichloromethane (100 ml). At −20° C. a 1 M solution of bis (trimethylsilyl)amide in tetrahydrofuran/cyclohexane (1/1 v/v) (1 equiv.) was added slowly and the mixture was stirred for 30 min. Methyl bromoacetate (4 ml) was subsequently added and the mixture was stirred for 2 h. at room temperature. Additional bis(trimethylsilyl)amide in tetrahydrofuran/cyclohexane (1/1 v/v) was added to force the reaction to completion. The mixture was diluted by dichloromethane and washed with 0.1N hydrochloric acid solution, water, 5% aqueous sodium bicarbonate solution and brine, dried over sodium sulphate, filtered and evaporated in vacuo. The residue was purified by chromatography on silica (eluent: heptane/ethyl acetate 6/4 v/v) to yield N-Boc-norLeu(cyclo)-Gly-OMe (12 g).

TLC: Rf=0.55, silica gel, ethyl acetate/heptane 6/4 v/v.

(c). BenzylSO$_2$-norLeu(cyclo)-Gly-OMe

N-Boc-norLeu(cyclo)-Gly-OMe (5.4 g) was dissolved in 50% TFA/dichloromethane 1/1 (v/v) (40 ml) and stirred for 1 h. at room temperature. The reaction mixture was evaporated in vacuo. The crude amine was dissolved in dichloromethane (40 ml), cooled (0° C.) and benzylsulphonyl chloride (3.43 g) was added. Triethylamine was added to keep the pH at 8 during the reaction. The mixture was stirred for 1 h. at room temperature, whereafter the mixture was concentrated in vacuo. The residue was dissolved in ethyl acetate and washed with 5% sodium hydrogencarbonate solution, water and brine, dried over sodium sulphate, filtered and evaporated in vacuo to yield BenzylSO$_2$-norLeu(cyclo)-Gly-OMe (6.1 g).

TLC: Rf=0.88, silica gel, dichloromethane/methanol 9/1 v/v.

(d). BenzylSO$_2$-norLeu(gyclo)-Gly-OH

A solution of BenzylSO$_2$-norLeu(cyclo)-Gly-OMe (6.1 g) in 100 ml of dioxane/water 9/1 was treated with sufficient 1

N sodium hydroxide to keep the pH at 13 for 2 hours at room temperature. After acidification, the mixture was poured into water and extracted with dichloromethane. The organic layer was washed with water and dried over sodium sulphate. Filtration followed by evaporaton of the solvent gave the desired compound (6.3 g).

TLC: Rf=0.73, silica gel, ethyl acetate/pyridine/acetic acid/water 63/20/6/11 v/v/v/v.

(e). BenzylSO$_2$-norLeu(cyclo)-Gly-LysininylΨ[COCO]—OH

The title compound was prepared according to the same procedures as described in example 3, starting from BenzylSO$_2$-norLeu(cyclo)-Gly-OH (385 mg) and H-Lysininyl(Cbz)Ψ[CHOHCO]—OMe. TFA (520 mg). The protected tripeptide (625 mg) was saponified, oxidized and deprotected (see example 4) to afford pure BenzylSO$_2$-norLeu(cyclo)-Gly-LysininylΨ[COCO]—OH (68 mg) as a diastereomeric mixture, after HPLC purification.

Rt(LC): 25.9 min, 20% A, 80% B to 20% A, 20% B and 80% C in 40 min.

Example 6

EthylSO$_2$-D-Cha-Pro-LysininylΨ[COCO]—OMe (a). Boc-D-Cha-Pro-OPac (-OPac=Phenacyl ester)

Boc-D-Cha-Pro-OPac was prepared according a similar manner, as described in example 2, using Boc-D-Cha-OH and H-Pro-OPac.

TLC: Rf=0.5, silica gel, dichloromethane/methanol 95/5 v/v.

(b). EthylSO$_2$-D-Cha-Pro-OPac

Boc-D-Cha-Pro-OPac (3.8 g) was dissolved in 50% TFA/dichloromethane (25 ml) and stirred for 30 minutes at room temperature. The reaction mixture was evaporated in vacuo. The crude amine was dissolved in dichloromethane (50 ml) and ethanesulphonyl chloride (0.8 ml) was added at −78° C. Triethylamine was added to keep the pH at 8 during the reaction. The mixture was stirred for 3 h at 0° C., whereafter water (25 ml) was added. After an additional stirring for 30 minutes at room temperature, the reaction mixture was concentrated in vacuo. The residue was dissolved in diethylether and washed with 1 N hydrochloric acid solution, water, 5% sodium hydrogencarbonate solution and brine, dried over sodium sulphate, filtered and evaporated in vacuo. Trituration of the crude material with methanol yielded EthylSO$_2$-D-Cha-Pro-OPac (3.0 g).

TLC: Rf=0.6, silica gel, dichloromethane/methanol 95/5 v/v.

(c). EthylSO$_2$-D-Cha-Pro-OH

To a solution of EthylSO$_2$-D-Cha-Pro-OPac (10 g) in tetrahydrofuran (250 ml) was added 1M solution of tetrabutylammonium fluoride in tetrahydrofuran (84 ml). The reaction mixture was stirred for 30 minutes at room temperature and poured into water (1l). The aqueous solution was extracted with ethyl acetate. The combined organic layers were successively washed with 1N hydrochloric acid solution and water, dried over sodium sulphate and concentrated in vacuo. The residue was purified by crystallisation from ethyl acetate/diisopropyl ether to yield EthylSO$_2$-D-Cha-Pro-OH (6.0 g).

TLC: Rf=0.2, silica gel, ethyl acetate/pyridine/acetic acid/water 163/20/6/11 v/v/v/v.

(d). EthylSO$_2$-D-Cha-Pro-LysininylΨ[COCO]—OMe

Coupling of EthylSO$_2$-D-Cha-Pro-OH (515 mg) and H-Lysininyl(Cbz)Ψ[CHOHCO]—OMe. TFA, as described in example 3(d), afforded the protected tripeptide (550 mg).

Oxidation followed by deprotection (see example 2) gave, after HPLC purification, the desired product (130 mg) as a mixture of diastereomers.

Rt (LC): 38.2 and 38.5 min, 20% A, 80% B to 20% A, 20% B and 60% C in 40 min.

Example 7

EthylSO$_2$-D-Cha-Pro-LysininylΨ[COCO]—OH

In analogy to example 6, EthylSO$_2$-D-Cha-Pro-LysininylΨ[CHOHCO]-OMe (550 mg) was assembled. Subsequent saponification, oxidation and deprotection, according to the methods as describe in example 3 and 2, afforded 180 mg EthylSO2-D-Cha-Pro-LysininylΨ[COCO]—OH (diastereomeric mixture) after HPLC purification.

Rt(LC): 35.7 and 36.0 min, 20% A, 80% B to 20% A, 20% B and 60% C.

Example 8

1-Piq-Pro-LysininylΨ[COCO]—OH (a). 2-Cbz-(4aR,8aR)-perhydroisoquinoline-1(R,S)-carboxylic acid(=N-(Cbz)-1-Piq-OH)

N-(Cbz)-1-Piq-OH has been synthesised as described in EP0643073, example 1.

TLC: Rf=0.85, silicagel, ethyl acetate/pyridine/acetic acid/water 63/20/6/11 v/v/v/v.

(b). N-(Cbz)-1-Piq-Pro-OH

Coupling of N-(Cbz)-1-Piq-OH (500 mg) and H-Pro-OtBu. (270 mg), according to the methods as described in example 2, yielded N-(Cbz)-1-Piq-Pro-OtBu (634 mg). Removal of the t-butyl ester was accomplished in a mixture of dichloromethane (1 ml), trifluoroacetic acid (3 ml), anisole (0.15 ml) for 1 h. at room temperature. The reaction mixture was concentrated in vacuo at low temperature and the residue was dissolved in water at pH of 9.5. The aqueous phase was washed with diethylether, whereafter the aqueous layer was acidified to pH 2.5 by 2M hydrochloric acid solution. The aqueous layer was extracted with ethyl acetate and the organic phase was washed with brine, dried over sodium sulphate and concentrated in vacuo to yield N-(Cbz)-1-Piq-Pro-OH (588 mg).

TLC: Rf=0.54, silica gel, ethyl acetate/pyridine/acetic acid/water 60/3/1/2 v/v/v/v.

(c). 1-Piq-Pro-LysininylΨ[COCO]—OH

N-(Cbz)-1-Piq-Pro-OH (478 mg) was coupled with the Lysininyl moiety according to the methods as described in example 3. The purified protected tripeptide (667 mg) was saponified, oxidized and deprotected (see example 2) to afford, after HPLC purification, a single isomer of 1-Piq-Pro-LysininylΨ[COCO]—OH (33 mg).

Rt(LC): 20.08 min, 20% A, 80% B to 20% A, 20% B and 60% C.

Example 9

HOOC—CH$_2$-D-Cha-Pro-LysininylΨ[COCO]—OH

According to the methods as described in example 3, 685 mg N-(t-Butyloxycarbonylmethyl)-N-Boc-D-Cha-Pro-OH (see example 1) was coupled to H-Lysininyl(Cbz)Ψ[CHOHCO]—OMe. TFA (see example 3c) whereafter the protected tripeptide (658 mg) was saponified, oxidized, deprotected and purified to yield 158 mg HOOC—CH2-D-Cha-Pro-LysininylΨ[COCO]—OH as a mixture of diastereomers.

Rt (LC): 22.3 min, 20% A, 80% B to 20% A, 20% B and 60% C.

Example 10

HOOC—CH$_2$-D-Cha-N-cyclopentyl-Gly-Lysininyl$\Psi$[COCO]—OH (a). N-cyclopentyl-Gly-OMe H-Gly-OMe.HCl (46.4 g) was dissolved in 400 ml methanol, cyclopentanone (34 g) and sodium cyanoborohydride (14 g) were added and the reaction was allowed to proceed for 16 h at room temperature. The reaction mixture was quenched with 6 M hydrochloric acid until pH 2 and stirred for 30 min at room temperature. The solvent was removed by evaporation under reduced pressure, the residu was dissolved in water and washed with diethylether. The pH was adjusted to pH>10 by additon of 6 M NaOH-solution, the product was extracted with dichloromethane, washed with brine, dried over sodium sulphate, filtered and concentrated under reduced pressure. The compound was crystallized from ethyl acetate as the HCl-salt. Yield: 43.5 g.

TLC: R$_f$=0.71, silica gel, ethyl acetate/pyridine/acetic acid/water 88/31/18/7 v/v/v/v.

(b). N-(t-Butyloxycarbonylmethyl)-N-Boc-D-Cha-N-cyclopentyl-Gly-OH

N-(t-Butyloxycarbonylmethyl)-N-Boc-D-Cha-N-cyclopentyl-Gly-OH was prepared according to the procedure described in example 1 for the dipeptide moiety, using N-(t-Butyloxycarbonylmethyl)-N-Boc-D-Cha-OH and N-cyclopentyl-Gly-OMe.

TLC: Rf=0.30, silica gel, dichloromethane/methanol 9/1 v/v.

(c). HOOC—CH$_2$-D-Cha-N-cyclopentyl-Gly-Lysininyl$\Psi$[COCO]—OH

According to the methods as described in example 3, N-(t-Butyloxycarbonylmethyl)-N-Boc-D-Cha-N-cyclopentyl-Gly-OH (547 mg) was coupled to H-Lysininyl(Cbz)$\Psi$[CHOHCO]—OMe.TFA (see example 3(c)) whereafter the protected tripeptide (660 mg) was saponified, oxidized, deprotected and purified to yield 212 mg HOOC—CH$_2$-D-Cha-N-cyclopentyl-Gly-Lysininyl$\Psi$[COCO]—OH as a mixture of diastereomers.

Rt (LC): 28.5 and 29.1 min, 20% A, 80% B to 20% A, 20% B and 60% C.

Example 11

HOOC—CH$_2$-D-Phe-Pro-Lysininyl$\Psi$[COCO]—OH

N-(t-Butyloxycarbonylmethyl)-N-Boc-D-Phe-Pro-OH was prepared according to the procedures described in example 19, using N-(t-Butyloxycarbonylmethyl)-N-Boc-D-Phe-OH and H-Pro-OBzl.HCl.

TLC: Rf=0.63, silica gel, ethyl acetate/pyridine/acetic acid/water 664/31/18/7 v/v/v/v.

HOOC—CH$_2$-D-Phe-Pro-Lysininyl$\Psi$[COCO]—OH

According to the methods described in example 3, 677 mg N-(t-Butyloxycarbonylmethyl)-N-Boc-D-Phe-Pro-OH was coupled with the H-Lysininyl(Cbz)$\Psi$[CHOHCO]—OMe.TFA whereafter the obtained tripeptide (814 mg) was saponified, oxidized, deprotected and purified by HPLC to give HOOC—CH$_2$-D-Phe-Pro-Lysininyl$\Psi$[COCO]—OH (284 mg) as a mixture of diastereomers.

Rt (LC): 16.1 and 17.0 min, 20% A, 80% B to 20% A, 20% B and 60% C.

Example 12

HOOC—CH$_2$-D-p-Cl-Phe-Pro-Lysininyl$\Psi$[COCO]—OH (a). N-(t-Butyloxycarbonylmethyl)-N-Boc-D-p-Cl-Phe-OH According to analogous procedures as described in example 1, H-D-p-Cl-Phe-OH. HCl (10 g) was converted into N-(t-Butyloxycarbonylmethyl)-N-Boc-D-p-Cl-Phe-OH. Yield: 16.7 g.

TLC: R$_f$=0.27, silica gel, ethyl acetate/methanol 9/1, v/v.

(b). N-(t-Butyloxcarbonylmethyl)-N-Boc-D-p-Cl-Phe-OSu (Su=succinimide)

A solution of N-(t-Butyloxycarbonylmethyl)-N-Boc-D-p-Cl-Phe-OH (14.67 g) in 250 ml acetonitrile was treated with N-hydroxysuccinimide (4.11 g) and 1-(3-dimethylaminopropyl)-3-ethylcarbodiimide hydrochloride (6.86 g) overnight at room temperature. The reaction mixture was evaporated to dryness and the residue was dissolved in ethyl acetate. The organic phase was washed with water, dried over sodium sulphate and concentrated to afford 19.11 g active ester, which was directly used in the next step.

(c). N-(t-Butyloxycarbonylmethyl)-N-Boc-D-p-Cl-Phe-Pro-OH

H-Pro-OH.HCl (10.79 g) was dissolved in 100 ml N,N-dimethylformamide and 100 ml water. The pH of the reaction mixture was adjusted to 8 with a 1 N sodium hydroxide solution, whereafter N-(t-Butyloxycarbonylmethyl)-N-Boc-D-p-Cl-Phe-OSu (19.11 g), dissolved in 120 ml of N,N-dimethylformamide, was added dropwise. The reaction was stirred overnight at room temperature at pH≈8. The reaction mixture was cooled and adjusted to pH≈2 with 1 N hydrochloric acid. The aqueous layer was extracted with dichloromethane. The organic phase was washed with water, dried over sodium sulphate en evaporated in vacuo. Silica gel purification, using a gradient ethyl acetate/methanol 9/1→1/1, afforded 7.04 g of the desired dipeptide.

TLC: R$_f$ 0.24, silica gel, ethyl acetate/methanol 8/2 v/v.

(d). HOOC—CH$_2$-D-p-Cl-Phe-Pro-Lysininyl$\Psi$[COCO]—OH

According to the methods described in example 3, N-(t-Butyloxycarbonylmethyl)-N-Boc-D-p-Cl-Phe-Pro-OH (500 mg) was coupled with H-Lysininyl(Cbz)$\Psi$[CHOHCO]—OMe.TFA, whereafter the obtained tripeptide (572 mg) was saponified, oxidized, deprotected and purified by HPLC to give HOOC—CH$_2$-D-p-Cl-Phe-Pro-Lysininyl$\Psi$[COCO]—OH (129 mg) as a mixture of diastereomers.

Rt (LC): 22.3 and 23.1 min. 20% A, 80% B to 20% A, 20% B and 60% C.

Example 13

HOOC—CH$_2$-D-Cha-Pro-Lysininyl$\psi$[COCO]—NH$_2$

N-(t-Butyloxycarbonylmethyl)-N-Boc-D-Cha-Pro-OH was prepared as described in example 1. Boc-Lysininyl(Cbz)$\psi$[CHOHCO]—OBu was prepared as described in example 3(b).

(a). Boc-Lysininyl(Cbz)$\psi$[CHOHCO]—OH

To a solution of Boc-Lysininyl(Cbz)$\psi$[CHOHCO]—OBu (320 mg) in a mixture of dioxane/water 9/1 v/v (11.2 ml) was added 1 ml of a 1N sodium hydroxide solution. The reaction mixture was stirred for 3 h at room temperature. The mixture was adjusted to pH 7 by adding 1N hydrochloric acid solution and most of the dioxane was removed by evaporation. The mixture was poured into cold water and extracted with ethyl acetate. The combined organic layers were washed with water, dried over magnesium sulphate, filtered and evaporated in vacuo yielding 308 mg Boc-Lysininyl(Cbz)$\psi$[CHOHCO]—OH.

TLC: R$_f$=0.46, silica gel, dichloromethane/methanol 8/2 v/v.

(b). Boc-Lysininyl(Cbz)$\psi$[CHOHCO]—NH$_2$

1-Hydroxy-benzotriazole hydrate (117 mg), N-methylmorpholine (132 μl), ammonium chloride (107 mg) and 1-(3-dimethylaminopropyl)-3-ethylcarbodiimide hydrochloride (186 mg) were added to a solution of Boc-Lysininyl(Cbz)ψ[CHOHCO]—OH (308 mg) in N,N-dimethylformamide (16.6 ml). The reaction mixture was stirred for 3 h at room temperature. The mixture was poured into water and extracted with ethyl acetate. The combined organic layers were washed with 1 N hydrochloric acid solution, water, 5% sodium hydrogen carbonate solution and water. The organic layer was dried over magnesium sulphate, filtered and evaporated. The residue was purified by chromatography on silica (eluent: gradient of dichloromethane/methanol 98/2 v/v to 96/4 v/v) to yield Boc-Lysininyl(Cbz)ψ[CHOHCO]—NH$_2$ (117 mg).

TLC: R$_f$=0.14, silica gel, dichloromethane/methanol 97/3 v/v.

(c). H-Lysininyl(Cbz)ψ[CHOHCO]—NH$_2$.TFA

H-Lysininyl(Cbz)ψ[CHOHCO]—NH2.TFA was prepared as described in example 1(h).

(d). N-(t-Butyloxycarbonylmethyl)-N-Boc-D-Cha-Pro-Lysininyl(Cbz)ψ[CHOHCO]-NH$_2$ 1-Hydroxy-benzotriazole hydrate (50 mg) and dicyclohexylcarbodiimide (60 mg) were added to a solution of N-(t-butyloxycarbonylmethyl)-N-Boc-D-Cha-Pro-OH (119.6 mg) in N,N-dimethylformamide (2 ml) at 0° C. The reaction mixture was stirred for ½ h at 0° C. A solution of H-Lysininyl(Cbz)ψ[CHOHCO]—NH$_2$.TFA (100 mg) in N,N-dimethylformamide (1 ml) of which the pH was adjusted to 8 with N,N-diisopropylethylamine, was added to the cold solution. After 1 h the mixture was allowed to warm to room temperature and was stirred overnight. The reaction mixture was cooled to −20° C., filtered and the filtrate was concentrated under reduced pressure. The residue was dissolved in ethyl acetate and washed with 5% sodium hydrogen carbonate solution, water, 2% citric acid aqueous solution and brine. The organic layer was dried over magnesium sulphate, filtered and evaporated. The residue was purified by chromatography on silica (eluent: gradient of dichloromethane/methanol 97/3 v/v to 95/5 v/v) to yield N-(t-butyloxycarbonylmethyl)-N-Boc-D-Cha-Pro-Lysininyl (Cbz)-ψ[CHOHCO]—NH$_2$ (93.5 mg).

TLC: R$_f$=0.34, silica gel, dichloromethane/methanol 95/5 v/v.

(e). N-(t-Butyloxycarbonylmethyl)-N-Boc-D-Cha-Pro-Lysininyl(Cbz)ψ[COCO]-NH$_2$

N-(t-Butyloxycarbonylmethyl)-N-Boc-D-Cha-Pro-Lysininyl(Cbz)ψ[COCO]—NH$_2$ was prepared as described in example 2(g). The mixture was washed with a sodium thiosulphate solution, 5% sodium hydrogen carbonate solution and water.

TLC: R$_f$=0.38, silica gel, dichloromethane/methanol 95/5 v/v.

(f). HOOC—CH$_2$-D-Cha-Pro-Lysininylψ[COCO]—NH$_2$

HOOC—CH$_2$-D-Cha-Pro-Lysininylψ[COCO]—NH$_2$ was prepared as described in example 2(h). The water layer was charged directly onto a preparative HPLC DeltaPak column using a gradient elution system of 20% A, 70% B, 10% C to 20% A, 30% B, 50% C over 40 min, at a flow rate of 50 ml/min.

(A: 0.5 M phosphate buffer pH 2.1, B: water, C: acetonitril/water=3/2 v/v) 87 mg N-(t-Butyloxycarbonylmethyl)-N-Boc-D-Cha-Pro-Lysininyl (Cbz)ψ[COCO]-NH$_2$ yielded 35 mg HOOC—CH$_2$-D-Cha-Pro-Lysininylψ[COCO]—NH$_2$.

Massa: CI$^+$: 478.4 [M−H]$^+$; CI$^−$: 476.4 [M−H]$^−$

R$_t$(LC): 21.10 and 21.41 min (diastereomeric mixture); 20% A, 80% B, 0% C to 20% A, 20% B, 60% C over 40 min.

Example 14

HOOC—CH$_2$-D-Cha-Pro-Lysininylψ[COCO]—OEt

N-(t-Butyloxycarbonylmethyl)-N-Boc-D-Cha-Pro-OH was prepared as described in example 1. Boc-Lysininyl (Cbz)ψ[CHOHCO]—OMe was prepared as described in example 3(b).

(a). H-Lysininyl(Cbz)ψ[CHOHCO]—OEt.HCl

Boc-Lysininyl(Cbz)ψ[CHOHCO]—OMe (2.14 g) was dissolved in a 3M hydrochloric acid solution in ethanol (100 ml) of −20° C. After the reaction mixture was stirred for 6 h at room temperature, it was concentrated in vacuo yielding H-Lysininyl(Cbz)ψ[CHOHCO]—OEt.HCl (2.36 g).

TLC: R$_f$=0.17 and R$_f$=0.25 (diastereomer mixture), silica gel, dichloromethane/methanol 95/5 v/v.

(b). N-(t-Butyloxycarbonylmethyl)-N-Boc-D-Cha-Pro-Lysininyl(Cbz)ψ[COHCO]—OEt

N-(t-Butyloxycarbonylmethyl)-N-Boc-D-Cha-Pro-Lysininyl(Cbz)ψ[COHCO]—OEt was prepared from H-Lysininyl(Cbz)ψ[CHOHCO]—OEt.HCl (2.40 g) and N-(t-butyloxycarbonyl-methyl)-N-Boc-D-Cha-Pro-OH (2.38 g) as described in example 13(d), but triethylamine was used instead of N,N-diisopropylethylamine. The crude product was purified by chromatography on silica (eluent: gradient of heptane/ethyl acetate 1/1 v/v to dichloromethane/methanol 97/3 v/v to 95/5 v/v) to yield N-(t-butyloxycarbonylmethyl)-N-Boc-D-Cha-Pro-Lysininyl (Cbz)ψ[COHCO]—OEt (1.24 g).

TLC: R$_f$=0.5, silica gel, dichloromethane/methanol 95/5 v/v.

(c). N-(t-Butyloxycarbonylmethyl)-N-Boc-D-Cha-Pro-Lysininyl(Cbz)ψ[COCO]—OEt

N-(t-Butyloxycarbonylmethyl)-N-Boc-D-Cha-Pro-Lysininyl(Cbz)ψ[COCO]—OEt was prepared as described in example 13(e).

TLC: R$_f$=0.51, silica gel, dichloromethane/methanol 97/3 v/v.

(d). HOOC—CH$_2$-D-Cha-Pro-Lysininylψ[COCO]—OEt

HOOC—CH$_2$-D-Cha-Pro-Lysininylψ[COCO]—OEt was prepared as described in example 13(f). The water layer was charged directly onto a preparative HPLC DeltaPak column using a gradient elution system of 20% A, 80% B, 0% C to 20% A, 54% B, 26% C over 45 min, at a flow rate of 80 ml/min.

(A: 0.5 M phosphate buffer pH 2.1, B: water, C: acetonitril/water=3/2 v/v) 293 mg N-(t-butyloxycarbonylmethyl)-N-Boc-D-Cha-Pro-Lysininyl (Cbz)ψ[COCO]—OEt yielded 62 mg HOOC—CH$_2$-D-Cha-Pro-Lysininylψ[COCO]—OEt.

Massa: ESI$^+$: 507.9 [MH]$^+$

R$_t$(LC): 26.45 and 27.30 min (diastereomer mixture): 20% A, 80% B, 0% C to 20% A, 20% B, 60% C over 40 min.

Example 15

HOOC—CH$_2$-D-Cha-Pro-Lysininylψ[COCO]-(1-azetidine)

N-(t-Butyloxycarbonylmethyl)-N-Boc-D-Cha-Pro-OH was prepared as described in example 1. N-(t-Butyloxycarbonylmethyl)-N-Boc-D-Cha-Pro-Lysininylψ [COCO]-(1-azetidine) was prepared in a similar manner as described in example 13, starting from Boc-Lysininyl(Cbz) Ψ[CHOHCO]—OBu. Deprotection (see example 13(f)) of 427 mg N-(t-butyloxycarbonylmethyl)-N-Boc-D-Cha-Pro-Lysininylψ[COCO]-(1-azetidine) gave, after HPLC purification, 105 mg product.

HPLC conditions: DeltaPak column using a gradient elution system of 20% A, 80% B, 0% C to 20% A, 45% B, 35% C over 45 min, at a flow rate of 80 ml/min.

(A: 0.5 M phosphate buffer pH 2.1, B: water, C: acetonitril/water 3/2 v/v)

Massa: FAB$^+$: 518.3 [M+H]$^+$; FAB$^-$: 516.2 [M+H]$^-$

R$_t$(LC): 26.24 and 26.70 min (diastereomer mixture): 20% A, 80% B, 0% C to 20% A, 20% B, 60% C over 40 min.

Example 16

HOOC—CH$_2$D-Cha-N-cyclopentyl-Gly-Lysininylψ [COCO]-(1-azetidine)

N-(t-Butyloxycarbonylmethyl)-N-Boc-D-Cha-N-cyclopentyl-glycine was prepared according to the procedure in example 1.

N-(t-Butyloxycarbonylmethyl)-N-Boc-D-Cha-N-cyclopentyl-Gly-Lysininylψ[COCO]-(1-azetidine) was prepared in a similar manner as described in example 15. Deprotection of 401 mg N-(t-butyloxycarbonylmethyl)-N-Boc-D-Cha-N-cyclopentyl-Gly-Lysininylψ[COCO]-(1-azetidine) gave, after HPLC purification, 107 mg of the product.

Massa: FAB$^+$: 546.2 [M+H]$^+$; FAB$^-$: 544.0 [M+H]$^-$

R$_t$(LC): 35.85 min: 20% A, 80% B, 0% C to 20% A, 20% B, 60% C over 40 min.

Example 17

HOOC—CH$_2$-D-Cha-Pro-Lysininylψ[COCO]—NHCH$_2$Ph

N-(t-Butyloxycarbonylmethyl)-N-Boc-D-Cha-Pro-OH was prepared as described in example 1. H-Lysininyl(Cbz)ψ[CHOHCO]—OMe.TFA was prepared as described in example 3(c).

(a). N-(t-Butyloxycarbonylmethyl)-N-Boc-D-Cha-Pro-Lysininyl(Cbz)ψ[CHOHCO]-OMe

N-(t-Butyloxycarbonylmethyl)-N-Boc D-Cha-Pro-Lysininyl(Cbz)ψ[CHOHCO]—OMe was prepared in a similar manner as described in example 13(d) from H-Lysininyl(Cbz)ψ[CHOHCO]—OMe.TFA (1.09 g) and N-(t-butyloxycarbonylmethyl)-N-BocD-Cha-Pro-OH (1.18 g). The crude product was purified by chromatography on silica (eluent: gradient of heptane/ethyl acetate 4/6 v/v to 3/7 v/v) to yield N-(t-butyloxycarbonylmethyl)-N-Boc-D-Cha-Pro-Lysininyl(Cbz)ψ[CHOHCO]—OMe (0.99 g).

TLC: R$_f$=0.5, silica gel, dichloromethane/methanol 95/5 v/v.

(b). N-(t-Butyloxycarbonylmethyl)-N-Boc-D-Cha-Pro-Lysininyl(Cbz)ψ[CHOHCO]-OH

To a solution of N-(t-butyloxycarbonylmethyl)-N-Boc-D-Cha-Pro-Lysininyl-(Cbz)ψ[CHOHCO]—OMe (0.98 g) in a mixture of dioxane/water 9/1 v/v (20 ml) was added 1 ml of a 1N sodium hydroxide solution. The mixture was poured into cold water, adjusted to pH 2 by adding a 1N hydrochloric acid solution and extracted with ethyl acetate. The combined organic layers were washed with water, dried over magnesium sulphate, filtered and evaporated in vacuo yielding 1.05 g N-(t-butyloxycarbonylmethyl)-N-Boc-D-Cha-Pro-Lysininyl(Cbz)ψ[CHOHCO]—OH.

TLC: R$_f$=0.4, silica gel, ethyl acetate/methanol 7/3 v/v.

(c). N-(t-Butyloxycarbonylmethyl)-N-Boc-D-Cha-Pro-Lysininyl(Cbz)ψ[CHOHCO]-NHCH$_2$Ph 1-Hydroxy-benzotriazole hydrate (150 mg), N-methylmorpholine (150 μl), benzylamine (155 μl) and 1-(3-dimethylaminopropyl)-3-ethylcarbodiimide hydrochloride (190 mg) were added to a solution of N-(t-butyloxycarbonylmethyl)-N-Boc-D-Cha-Pro-Lysininyl (Cbz)ψ[CHOHCO]—OH (502 mg) in N,N-dimethylformamide (16.6 ml). The reaction mixture was stirred for 17 h at room temperature. The mixture was poured into a cold 1 N hydrochloric acid solution and extracted with ethyl acetate. The combined organic layers were washed with, water, 5% sodium hydrogen carbonate solution and water. The organic layer was dried over magnesium sulphate, filtered and evaporated to yield N-(t-butyloxycarbonylmethyl)-N-Boc-D-Cha-Pro-Lysininyl (Cbz)ψ[CHOHCO]—NHCH$_2$Ph (512.4 mg).

TLC: R$_f$=0.5, silica gel, dichloromethane/methanol 95/5 v/v.

(d). N-(t-Butyloxycarbonylmethyl)-N-Boc-D-Cha-Pro-Lysininyl(Cbz)ψ[COCO]-NHCH$_2$Ph N-(t-Butyloxycarbonylmethyl)-N-Boc-D-Cha-Pro-Lysininyl(Cbz)ψ[COCO]—NHCH$_2$Ph was prepared as described in example 13(e).

TLC: R$_f$=0.32, silica gel, dichloromethane/methanol 97/3 v/v.

(e). HOOC—CH$_2$-D-Cha-Pro-Lysininylψ[COCO]—NHCH$_2$Ph

HOOC—CH$_2$-D-Cha-Pro-Lysininylψ[COCO]—NHCH$_2$Ph was prepared as described in example 13(f).

R$_t$(LC): 39.05 min: 20% A, 80% B, 0% C to 20% A, 20% B, 60% C over 40 min.

Example 18

HOOC—CH$_2$-D-Cha-Pro-Lysininylψ[COCO]—N(CH$_3$)$_2$

HOOC—CH$_2$-D-Cha-Pro-Lysininylψ[COCO]—N(CH$_3$)$_2$ was prepared in a similar manner as described in example 17, starting from N-(t-butyloxycarbonylmethyl)-N-Boc-D-Cha-Pro-Lysininyl(Cbz)ψ[CHOHCO]—OH.

R$_t$(LC): 32.84 min: 20% A, 80% B, 0% C to 20% A, 20% B, 60% C over 40 min.

Example 19

HOOC—CH$_2$-D-Dpa-Pro-Lysininyl-(2-thiazolyl)

(a). Boc-D-Dpa-Pro-OBzl

To a cold (0° C.) solution of Boc-D-Dpa-OH (5.2 g) in N,N-dimethylformamide (50 ml) were successively added 1-hydroxy benzotriazole (3.1 g), dicyclohexyl carbodiimide (3.3 g), H-Pro-OBzl.HCl (4.07 g) and triethylamine (2.46 ml). The mixture was stirred at 0° C. for 1 hour and then kept at room temperature overnight. The mixture was cooled to −20° C. and dicyclohexylurea was removed by filtration. The filtrate was evaporated to dryness. The residue was dissolved in ethyl acetate and washed successively with 5% sodium hydrogen carbonate, water and brine, dried over sodium sulphate and concentrated in vacuo. The residue was chromatographed on silica gel (eluent: heptane/ethyl acetate 4/6 v/v) yielding Boc-D-Dpa-Pro-OBzl (8.7 g).

TLC: R$_f$=0.95, silica, ethyl acetate/pyridine/acetic acid/water 520/31/18/7 v/v/v/v.

(b). Boc-D-Dpa-Pro-OH

10% palladium on charcoal (1 g) was added to a solution of Boc-D-Dpa-Pro-OBzl (7.0 g) in methanol (140 ml). The mixture was hydrogenated at atmospheric pressure at room temperature for 1 hour. The palladium catalyst was removed by filtration and the solvent was removed by evaporation at reduced pressure yielding Boc-D-Dpa-Pro-OH (5.5 g).

TLC: R$_f$=0.59, silica, ethyl acetate/pyridine/acetic acid/water 520/31/18/7 v/v/v/v.

(c). Boc-D-Dpa-Pro-Lysininyl-(2-thiazolyl)

The mixed anhydride coupling between Boc-D-Dpa-Pro-OH and H-Lysininyl(Cbz)-(2-thiazolyl).TFA (see example 1) was done according to the procedures described in example 22, yielding N-Boc-D-Dpa-Pro-Lysininyl-(2-thiazolyl) (560 mg).

TLC: $R_f$=0.1, silica, toluene/ethyl acetate 3/7 v/v.

(d). H-D-Dpa-Pro-Lysininyl(Cbz-(2-thiazolyl).TFA

N-Boc-D-Dpa-Pro-Lysininyl-(2-thiazolyl) (560 mg) was dissolved in dry dichloromethane (2.5 ml) and trifluoroacetic acid (2.5 ml) and stirred for 1 h at room temperature. The solution was concentrated in vacuo and coevaporated with toluene yielding H-D-Dpa-Pro-Lys(Cbz)-(2-thiazolyl).TFA (670 mg).

TLC: $R_f$=0.51, silica, toluene/ethyl acetate 1/1 v/v.

(e). N-(t-Butyloxycarbonylmethyl)-D-Dpa-Pro-Lysininyl (Cbz)-(2-thiazolyl

H-D-Dpa-Pro-Lys(Cbz)-(2-thiazolyl).TFA (570 mg) was dissolved in acetonitrile (10 ml), tert.-butyl bromoacetate (141 µl) was added. The solution was kept at pH 8 with N,N-diisopropylethylamine and stirred for 2 days at room temperature. The reaction mixture was concentrated in vacuo, dissolved in ethyl acetate, washed with water and brine, dried on magnesium sulphate and again concentrated. The residue was chromatographed on silica using ethyl acetate/toluene 1/4 as eluent yielding N-(t-Butyloxycarbonylmethyl)-D-Dpa-Pro-Lysininyl(Cbz)-(2-thiazolyl) (499 mg).

TLC: $R_f$=0.47, silica, dichloromethane/methanol 96/4 v/v/v.

(f). HOOC—CH$_2$-D-Dpa-Pro-Lysininyl-(2-thiazolyl)

The deprotection and the purification of N-(t-Butyloxycarbonylmethyl)-D-Dpa-Pro-Lysininyl-(Cbz)-(2-thiazolyl) were done according to the procedures described in example 22. Yield of a mixture of two diastereomers: 177 mg.

R$_t$(LC): 32.57 and 33.22 min, 20% A and 80% B to 20%A, 20%B and 60% C in 40 min.

Example 20

HOOC—CH$_2$-D-Cha-N-cyclopentyl-Gly-Lysininylψ [COCO]—NH$_2$

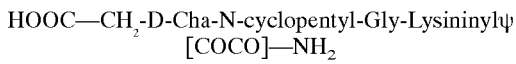

N-(t-Butyloxycarbonylmethyl)-N-Boc-D-Cha-N-cyclopentyl-glycine was prepared according to the procedure for the preparation of the dipeptide in example 1.

N-(t-Butyloxycarbonylmethyl)-N-Boc-D-Cha-N-cyclopentyl-Gly-Lysininylψ[COCO]-NH$_2$ was prepared in a similar manner as described in example 13, starting from Boc-Lysininyl(Cbz)ψ[CHOHCO]—OMe.

R$_t$(LC): 34.09 min: 20% A, 80% B, 0% C to 20% A, 20% B, 60% C over 40 min.

Example 21

HOOC—CH$_2$-D-Cha-Pro-Lysininylψ[COCO]— NHCH$_3$

HOOC—CH$_2$-D-Cha-Pro-Lysininylψ[COCO]—NHCH$_3$ was prepared in a similar manner as described in example 17, starting from N-(t-butyloxycarbonylmethyl)-N-Boc-D-Cha-Pro-Lysininyl(Cbz)ψ[CHOHCO]—OH.

R$_t$(LC): 29.61 min: 20% A, 80% B, 0% C to 20% A, 20% B, 60% C over 40 min.

Example 22

N-Me-D-Nle-Pro-Lysininyl-(2-thiazolyl)

(a). H-D-Nle-OMe. HCl

To 270 ml of methanol, cooled to −15° C., 18.2 g thionylchloride was added. Subsequently, the temperature was allowed to rise to −10° C. than kept constant for 20 min after which 10 g H-D-Nle-OH was added. The temperature was slowly increased and at reflux kept constant for 5 h. The product was crystallized from methanol and diethylether at 4° C. and this yielded 12.9 g.

TLC: $R_f$=0.61, silica, n-butanol/acetic acid/water 10/1/3 v/v/v.

(b). Boc-D-Nle-OMe

H-D-Nle-OMe.HCl (12.9 g) was dissolved in 200 ml dry methanol followed by addition of di-tert-butyl dicarbonate (15.5 g) and triethylamine (19.8 ml). The reaction was stirred for 3h at room temperature after which the mixture was concentrated in vacuo. Next, the residue was dissolved in ethyl acetate and washed with water. The product was chromatographed on silica using heptane/ethyl acetate 3/1 v/v. Yield: 16.9 g.

TLC: $R_f$=0.55, silica, heptane/ethyl acetate 3/1 v/v.

(c). N-Me-Boc-D-Nle-OMe

Boc-D-Nle-OMe (16.9 g) was dissolved in 200 ml dry N,N-dimethylformamide under nitrogen. Next, methyliodide (24.9 ml) was added, cooled to 0° C., sodium hydride (3.31 g, 60% dispersion in oil) was added and the mixture was allowed to react during 16 h at room temperature. The mixture was concentrated in vacuo, dissolved in ethyl acetate, washed with 0.1 N hydrochloric acid, water, sodium bicarbonate (5%) and water, dried and concentrated again. This yielded 18.8 g of alkylated product.

TLC: $R_f$=0.56, silica, heptane/ethyl acetate 3/1 v/v.

(d). N-Me-Boc-D-Nle-OH

N-Me-Boc-D-Nle-OMe (18 g) was dissolved in 400 ml dioxane/water 9/1 (v/v) and the pH of the solution was adjusted to 12 with 1N NaOH. The reaction was allowed to proceed for 2 h, keeping the pH constant at 12. The work-up procedure involved acidification with hydrochloric acid, cooling on ice, adding extra water (400 ml) and extraction with dichloromethane. The organic layer was washed with brine, dried, filtered and concentrated in vacuo. This yielded 18.9 g.

TLC: $R_f$=0.26, silica, dichloromethane/methanol 9/1 v/v.

(e). N-Me-Boc-D-Me-Pro-OH

First the N-succinimide ester was prepared starting from N-Me-Boc-D-Nle-OH. 18 g of this derivative was dissolved in acetonitrile (250 ml) and 1-ethyl-3-[3-(dimethylamino) propyl]-carbodiimide hydrochloride (EDCI) (14.5 g) and N-hydroxy-succinimide (HONSu) (8.7 g) were added. The reaction required 16 h at room temperature after which the solvent was removed, the residue was dissolved in ethyl acetate and washed with water and dried. This yielded 24.3 g of crude ONSu ester. The next step was to dissolve proline.HCl (20.9 g) in 300 ml N,N-dimethylformamide and 300 ml water and the pH was adjusted to 8 with 2 N NaOH solution. A solution of the ONSu ester (24.3 g in 300 ml N,N-dimethylformamide) was added dropwise to this solution at the pH of 8. The reaction was completed after 5 h, after which the organic solvent was largely removed by evaporation under reduced pressure. Extra water (300 ml) was added and the mixture was acidified. The product was extracted with ethyl acetate and washed with water. After drying, filtration and concentration the product was obtained as a yellow oil in 22.2 g. The crude product was chromatographed on silica using ethyl acetate/methanol 8/2 v/v as eluent. Yield: 13.2 g.

TLC: $R_f$=0.65, silica, ethyl acetate/pyridine/acetic acid/ water=163/20/6/11 v/v/v/v.

(f). N-Me-Boc-D-Nle-Pro-Lysininyl(Cbz)-(2-thiazolyl)

N-Me-Boc-D-Me-Pro-OH (376 mg) was dissolved in dry N,N-dimethylformamide (3 ml). After addition of N,N- diisopropylethylamine (0.19 ml), the reaction mixture was placed under nitrogen and cooled to −20° C. Isobutyl chloroformate (136 µl) was subsequently added and the mixture was allowed to stir for 15 min at −20° C. H-Lysininyl(Cbz)-(2-thiazolyl).TFA (see example 1) was dissolved in dry N,N-dimethylformamide (3 ml) and added dropwise to the cold mixed anhydride solution, maintaining the pH at 8.5 by addition of N,N-diisopropylethylamine. The reaction mixture was stirred for 15 min at −20° C. and 1h. at room temperature. The reaction mixture was evaporated to dryness. The residue was dissolved in ethyl acetate and successively washed with 5% aqueous sodium bicarbonate solution, water and brine, dried over sodium sulphate and concentrated in vacuo. The residue was purified by chromatography on silica (eluent: ethyl acetate/heptane 1/1 v/v) to yield Boc-N-Me-D-Nle-Pro-Lysininyl(Cbz)-(2-thiazolyl) (408 mg).

TLC: $R_f$=0.21, silica, ethyl acetate/heptane 1/1 v/v.

(g). N-Me-D-Nle-Pro-Lysininyl-(2-thiazolyl)

Boc-N-Me-D-Nle-Pro-Lysininyl(Cbz)-(2-thiazolyl) (408 mg) was prepared according the procedure described in example 1p. The crude product was charged onto a preparative HPLC Deltapack C18 RP column using a gradient elution system of 20% A/80%B to 20% A/30% B/50% C over 40 minutes, at a flow rate of 80 ml/min.

Yield of two diastereomers:

105 mg. $R_t$(LC): 19.17 min, 20% A, 80% B to 20% A, 20% Band 60% C in 40 min.

110 mg. $R_t$(LC): 21.47 min, 20% A, 80% B to 20% A, 20% Band 60% C in 40 min.

Example 23

N-Me-D-Phe-Pro-Lysininyl-(2-thiazolyl (a). N-Me-Boc-D-Phe-Pro-OH

The synthesis of N-Me-Boc-D-Phe-Pro-OH starting with H-D-Phe-OH was done according to the procedures described in example 2.

(b). N-Me-D-Phe-Pro-Lysininyl-(2-thiazolyl)

The mixed anhydride coupling between N-Me-Boc-D-Phe-Pro-OH and H-Lysininyl(Cbz)-(2-thiazolyl).TFA (see example 1), the deprotection and the purification were done according to the procedures described in example 22.

Yield of two diastereomers:

89 mg. $R_t$(LC): 8.45 min, 20% A,60% B and 20% C to 100% C in 40 min.

63 mg. $R_t$(LC): 10.98 min, 20% A, 60% B and 20% C to 100% C in 40 min.

Example 24

N-Me-D-Cha-Pro-Lysininyl-(2-thiazolyl)

(a). N-Me-Boc-D-Cha-Pro-OH

The synthesis of N-Me-Boc-D-Cha-Pro-OH starting with H-D-Cha-OH was done according to the procedures described in example 3.

(b). N-Me-D-Cha-Pro-Lysininyl-(2-thiazolyl)

The mixed anhydride coupling between N-Me-Boc-D-Cha-Pro-OH and H-Lysininyl(Cbz)-(2-thiazolyl).TFA (see example 1), the deprotection and the purification were done according to the procedures described in example 22.

Yield of two diastereomers:

140 mg. $R_t$(LC): 12.93 min, 20% A, 60% B and 20% C to 100% C in 40 min.

139 mg. $R_t$(LC): 14.31 min, 20% A, 60% B and 20% C to 100% C in 40 min.

Example 25

EthylSO$_2$-D-Cha-Pro-Lysininyl-(2-thiazolyl)

(a). EthylSO$_2$-D-Cha-Pro-OH

The synthesis of EthylSO$_2$-D-Cha-Pro-OH starting with Boc-D-Cha-OH and H-Pro-OPac was done according to the procedures described in example 6.

(b). EthylSO$_2$-D-Cha-Pro-Lysininyl-(2-thiazolyl)

The mixed anhydride coupling between EthylSO$_2$-D-Cha-Pro-OH and H-Lysininyl(Cbz)-(2-thiazolyl).T FA (see example 1), the deprotection and the purification were done according to the procedures described in example 22.

Yield of diastereomers: 127 mg.

$R_t$(LC): 44.52 and 45.58 min, 20% A, 80% B to 20% A, 20% B and 60% C in 40 min.

Example 26

2-Propylpentanoyl-Asp(OMe)-Pro-Lysininyl-(2-thiazolyl)

(a). Boc-Asp(OMe)-OH

H-Asp(OMe)-OH (10.0 g) was dissolved in dioxane/water 2/1 (150 ml) and cooled in ice. Sodium bicarbonate (4.6 g) and di-tert-butyl dicarbonate (13.1 g) were added in portions. The mixture was stirred for 16 h, while the pH was kept at 8.5 with sodium bicarbonate. Water (400 ml) was added and the mixture was washed extensively with heptane, cooled in ice, acidified with 1 N hydrochloric acid to pH 2.5 and extracted with ethyl acetate (300 ml). The organic layer was washed with water and brine, dried over sodium sulphate, filtered and evaporated in vacuo yielding Boc-Asp(OMe)-OH (10.25 g).

TLC: $R_f$=0.58, silica, ethyl acetate/pyridine/acetic acid/water 163/20/6/11 v/v/v/v.

(b). Boc-Asp(OMe)-Pro-OBzl

Boc-Asp(OMe)-Pro-OBzl has been synthesised as described in WO 95/35312, example 1, replacing N-methylmorpholine by N-ethylmorpholine.

TLC: $R_f$=0.40, silica, dichloromethane/methanol 95/5 v/v.

(c). H-Asp(OMe)-Pro-OBzl.HCl

Boc-Asp(OMe)-Pro-OBzl (7.25 g) was dissolved in dry ethyl acetate (25 ml) and cooled in ice. Ethyl acetate saturated with hydrochloric acid (45 ml) was added and the mixture was stirred at 0° C. for 5 h. The excess of hydrochloric acid was removed by a nitrogen-flow and the resulting solution was concentrated in vacuo yielding H-Asp(OMe)-Pro-OBzl.HCl as a white solid (6.21 g).

TLC: $R_f$=0.17, silica, dichloromethane/methanol 95/5 v/v.

(d). 2-Propylpentanoyl-Asp(OMe)-Pro-OBzl

A solution of H-Asp(OMe)-Pro-OBzl.HCl (6.21 g), dry dichloromethane (10 ml) and N,N-diisopropylethylamine (200 µl) was added at 0° C. to a solution of 2-propylpentanoic acid anhydride which has been prepared by dissolving 2-propyl-pentanoic acid (1.63 ml) in dry dichloromethane (15 ml), cooling in ice, adding 1,3-dicyclohexylcarbodiimide (1.11 g) and stirring of this solution for 5 min. The mixture was stirred at room temperature, maintaining the pH at 8.5 by addition of N,N-diisopropylethylamine, for 16 h after which 0.5 eq of 2-propylpentanoic acid anhydride was added and the solution was stirred for another 4 h. Then 1,3-dicyclohexylurea was removed by filtration. The filtrate was concentrated in vacuo and the residue was dissolved in ethyl acetate. This solution was washed successively with 1N hydrochloric acid, saturated sodium hydrogencarbonate and brine, dried over sodium sulphate and concentrated in vacuo. The residue was purified by chromatography on silica using toluenelethyl acetate 8/2 v/v as eluent yielding 2-propylpentanoyl-Asp(OMe)-Pro-OBzl (6.54 g).

TLC: $R_f$=0.65, silica, dichloromethane/methanol 95/5 v/v.

(e). 2-Propylpentanoyl-Asp(OMe)-Pro-OH

10% palladium on charcoal (750 mg) was added to a solution of 2-propylpentanoyl-Asp(OMe)-Pro-OBzl (705 mg) in methanol (10 ml). The mixture was hydrogenated at atmospheric pressure at room temperature for 2 hour. The palladium catalyst was removed by filtration and the solvent was removed by evaporation at reduced pressure yielding 2-propylpentanoyl-Asp(OMe)-Pro-OH (580 mg).

TLC: $R_f$=0.48, silica, ethyl acetate/pyridine/acetic acid/water 163/20/6/11 v/v/v/v.

(f). 2-Propylpentanoyl-Asp(OMe)-Pro-Lysininyl-(2-thiazolyl)

The mixed anhydride coupling between 2-propylpentanoyl-Asp(OMe)-Pro-OH and H-Lysininyl(Cbz)-(2-thiazolyl).TFA (see example 1), the deprotection and the purification were done according to the procedures described in example 22.

Yield of a mixture of two diastereomers: 186 mg. $R_t$(LC): 23.16 and 24.30 min, 20% A, 60% B and 20% C to 100% C in 40 min.

Example 27

1-Piq-Pro-Lysininyl-(2-thiazolyl)

(a). 1-Piq-Pro-OH

The synthesis of 1-Piq-Pro-OH was done according to the procedures described in example 8.

(b). 1-Piq-Pro-Lysininyl-(2-thiazolyl)

The mixed anhydride coupling between 1-Piq-Pro-OH and H-Lysininyl(Cbz)-(2-thiazolyl).TFA (see example 1), the deprotection and the purification were done according to the procedures described in example 22.

Yield of two diastereomers:

92 mg. $R_t$(LC): 23.75 min, 20% A, 80% B to 20% A, 20% B and 60% C in 40 min.

97 mg. $R_t$(LC): 25.72 min, 20% A, 80% B to 20% A, 20% B and 60% C in 40 min.

Example 28

HOOC—$CH_2$-D-Cha-N-cylopentyl-Gly-Lsininyl-(2-thiazolyl)

(a). N-(t-Butyloxycarbonylmethyl)-N-Boc-D-Cha-N-cyclopentyl-Gly-OH

The synthesis of N-(t-Butyloxycarbonylmethyl)-N-Boc-D-Cha-N-cyclopentyl-Gly-OH starting with H-D-Cha-OH.HCl was done according to the procedures described in example 10.

(b). HOOC—$CH_2$-D-Cha-N-cyclopentyl-Gly-Lysininyl-(2-thiazolyl)

The mixed anhydride coupling between N-(t-Butyloxycarbonylmethyl)-N-Boc-D-Cha-N-cyclopentyl-Gly-OH and H-Lysininyl(Cbz)-(2-thiazolyl).TFA (see example 1), the deprotection and the purification were done according to the procedures described in example 22.

Yield of a mixture of two diastereomers:

107 mg. $R_t$(LC): 20.39 and 20.82 min, 20% A, 60% B and 20% C to 100% C in 40 min.

Example 29

HOOC—$CH_2$-D-Phe-Pro-Lysininyl-(2-thiazolyl)

(a). N-(t-Butyloxycarbonylmethyl)-N-Boc-D-Phe-Pro-OH

The synthesis of N-(t-Butyloxycarbonylmethyl)-N-Boc-D-Phe-Pro-OH starting from H-D-Phe-OH.HCl was done according to the procedures described in example 11.

(b). HOOC—$CH_2$-D-Phe-Pro-Lysininy1-(2-thiazolyl)

The mixed anhydride coupling between N-(t-Butyloxycarbonylmethyl)-N-Boc-D-Phe-Pro-OH and H-Lysininyl(Cbz)-(2-thiazolyl).TFA (see example 1); the deprotection and the purification were done according to the procedures described in example 22.

Yield of two diastereomers:

143 mg. $R_t$(LC): 24.98 min, 20% A, 80% B to 20% A, 20% B and 60% C in 40 min.

149 mg. $R_t$(LC): 26.91 min, 20% A, 80% B to 20% A, 20% B and 60% C in 40 min.

Example 30

HOOC—$CH_2$-D-p-Cl-Phe-Pro-Lysininyl-(2-thiazolyl)

(a). N-(t-Butyloxycarbonylmethyl)-N-Boc-D-p-Cl-Phe-Pro-OH

The synthesis of N-(t-Butyloxycarbonylmethyl)-N-Boc-D-p-Cl-Phe-Pro-OH starting from H-D-p-Cl-Phe-OH.HCl was done according to the procedures described in example 12.

(b). HOOC—$CH_2$-D-p-Cl-Phe-Pro-Lysininyl-(2-thiazolyl)

The mixed anhydride coupling between N-(t-Butyloxycarbonylmethyl)-N-Boc-D-p-Cl-Phe-Pro-OH and H-Lysininyl(Cbz)-(2-thiazolyl).TFA (see example 1), the deprotection and the purification were done according to the procedures described in example 22.

Yield of a mixture of two diastereomers:

187 mg. $R_t$(LC): 28.86 and 30.63 min, 20% A and 80% B to 20%A, 20%B and 60% C in 40 min.

Example 31

Further, the following compounds can be prepared by using the methods of the present invention:

HOOC—$CH_2$-D-Cha-Pec-Lysininyl$\Psi$[COCO]—OH
HOOC—$CH_2$-D-Cha-Pec-Lysininyl-(2-thiazolyl)
HOOC—$CH_2$-D-Cha-(N-cyclohexyl)-Gly-Lysininyl$\Psi$[COCO]—OH
HOOC—$CH_2$-D-Cha-(N-cyclohexyl)-Gly-Lysininyl-(2-thiazolyl)
HOOC—$CH_2$-D-Cha-(N-cyclopropyl)-Gly-Lysininyl$\Psi$[COCO]—OH
HOOC—$CH_2$-D-Cha-(N-cyclopropyl)-Gly-Lysininyl-(2-thiazolyl)
N-Me-D-Phe-(N-cyclopentyl)-Gly-Lysininyl$\Psi$[COCO]—OH
N-Me-D-Phe-(N-cyclopentyl)-Gly-Lysininyl-(2-thiazolyl)
2-propyl-pentanoyl-Asp(OMe)-Pro-Lysininyl$\Psi$[COCO]—OH
2-propyl-pentanoyl-Asp-Pro-Lysininyl$\Psi$[COCO]—OH
2-propyl-pentanoyl-Asp-Pro-Lysininyl-(2-thiazolyl)
2-hydroxy-3-cyclohexyl-propionyl-Pro-Lysininyl$\Psi$[COCO]—OH
2-hydroxy-3-cyclohexyl-propionyi-Pro-Lysininyl-(2-thiazolyl)
1-Piq-(N-cyclopentyl)-Gly-Lysininyl$\Psi$[COCO]—OH
1-Piq-(N-cyclopentyl)-Gly-Lysininyl-(2-thiazolyl)
Diphenylpropionyl-Pro-Lysininyl-(2-thiazolyl)
N-Me-D-Nle-Pro-Lysininyl$\Psi$[COCO]—OH
EthylSO$_2$-D-Phe-Pro-Lysininyl$\Psi$[COCO]—OH
EthylSO$_2$-D-Phe-Pro-Lysininyl-(2-thiazolyl)
EthylSO$_2$-N(Me)-D-Cha-Pro-Lysininyl$\Psi$[COCO]—OH
EthylSO$_2$-N(Me)-D-Cha-Pro-Lysininyl-(2-thiazolyl)
EthylSO$_2$-N(Me)-D-Cha-Pro-Lysininyl-(2-oxazolyl)
HOOC—$CH_2$-N(Me)-D-Cha-Pro-Lysininyl$\Psi$[COCO]—OH HOOC—CH₂-N(Me)-D-Cha-Pro-Lysininyl-(2-thiazolyl)
HOOC—CH₂-N(Me)-D-Cha-Pro-Lysininyl-(2-oxazolyl)

Example 32
Anti-thrombin Assay

Thrombin (Factor IIa) is a factor in the coagulation cascade. The anti-thrombin activity of compounds of the present invention was assessed by measuring spectrophotometrically the rate of hydrolysis of the chromogenic substrate s-2238 exterted by thrombin. This assay for anti-thrombin activity in a buffer system was used to assess the $IC_{50}$-value of a test compound.

Test medium: Tromethamine-NaCl-polyethylene glycol 6000 (TNP) buffer. Reference compound: 12581 (Kabi) Vehicle: TNP buffer. Solubilisation can be assisted with dimethylsulphoxide, methanol, ethanol, acetonitrile or tert-butyl alcohol which are without adverse effects in concentrations up to 2.5% in the final reaction mixture.

Technique

Reagents*: 1. Tromethamine-NaCl (TN) buffer. Composition of the buffer: Tromethamine (Tris) 6.057 g (50 mmol), NaCl 5.844 g (100 mmol), water to 1 l. The pH of the solution is adjusted to 7.4 at 37° C. with HCl (10 mmol·l⁻¹). 2. TNP buffer: Polyethylene glycol 6000 is dissolved in TN buffer to give a concentration of 3 g·l⁻¹. 3. S-2238 solution: One vial S-2238 (25 mg; Kabi Diagnostica, Sweden) is dissolved in 20 ml TN buffer to give a concentration of 1.25 mg·ml⁻¹ (2 mmol·l⁻¹). 4. Thrombin solution: Human thrombin (16 000 nKat·vial⁻¹; Centraal Laboratorium voor Bloedtransfusie, Amsterdam, The Netherlands) is dissolved in TNP buffer to give a stock solution of 835 nKat·ml⁻¹. Immediately before use this solution is diluted with TNP buffer to give a concentration of 3.34 nKat·ml⁻¹.

* All ingredients used are of analytical grade
For aqueous solutions ultrapure water (Milli-Q quality) is used.

Preparation of Test and Reference Compound Solutions

The test and reference compounds are dissolved in Milli-Q water to give stock concentrations of 10⁻² mol·l⁻¹. Each concentration is stepwise diluted with the vehicle to give concentrations of 10⁻³, 10⁻⁴ and 10⁻⁵ mol·l⁻¹. The dilutions, including the stock solution, are used in the assay (final concentrations in the reaction mixture: 3·10⁻³; 10⁻³; 3·10⁻⁴; 10⁻⁴; 3·10⁻⁵; 10⁻⁵; 3·10⁻⁶ ; and 10⁻⁶ mol·l⁻¹, respectively).

Procedure

At room temperature 0.075 ml and 0.025 ml test compound or reference compound solutions or vehicle are alternately pipetted into the wells of a microtiter plate and these solutions are diluted with 0.115 ml and 0.0165 ml TNP buffer, respectively. An aliquot of 0.030 ml S-2238 solution is added to each well and the plate is pre-heated and pre-incubated with shaking in an incubator (Amersham) for 10 min. at 37° C. Following pre-incubation the hydrolysis of S-2238 is started by addition of 0.030 ml thrombin solution to each well. The plate is incubated (with shaking for 30 s) at 37° C. Starting after 1 min of incubation, the absorbance of each sample at 405 nm is measured every 2 min. for a period of 90 min. using a kinetic microtiter plate reader (Twinreader plus, Flow Laboratories).

All data are collected in an IBM personal computer using LOTUS-MEASURE. For each compound concentration (expressed in mol·l⁻¹ reaction mixture) and for the blank the absorbance is plotted versus the reaction time in min.

Evaluation of responses: For each final concentration the maximum absorbance was calculated from the assay plot. The $IC_{50}$-value (final concentration, expressed in μmol·l⁻¹, causing 50% inhibition of the maximum absorbance of the blank) was calculated using the logit transformation analysis according to Hafner et al. (Arzneim.-Forsch./Drug Res. 1977; 27(II): 1871-3).

In the following table, $IC_{50}$-values of compounds of the invention are listed:

| Example | $IC_{50}$-value (μM) |
|---------|----------------------|
| 1       | 0.56                 |
| 3       | 4.3                  |
| 11      | 5                    |
| 15      | 0.7                  |
| 27      | 4.64                 |
| 30      | 5.1                  |

I claim:

1. A serine protease inhibitor compound having the Formula I

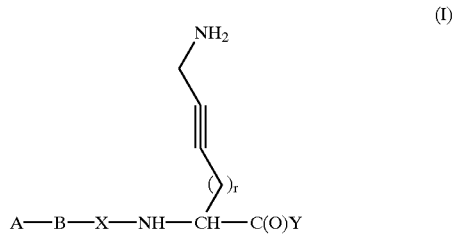

wherein

A is H, substituted or unsubstituted D,L α-hydroxyacetyl, $R^1$, $R^1$—O—C(O)—, $R^1$—C(O)—, $R^1$—SO₂—, $R^2OOC$—(CHR²)ₘ—SO₂—, $R^2OOC$—(CHR²)ₘ—, H₂NCO—(CHR²)ₘ—, or an N-protecting group, wherein $R^1$ is selected from (1–12C)alkyl, (2–12C)alkenyl, (2–12C)alkynyl and (3–8C)cycloalkyl, which groups may be substituted with (3–8C)cycloalkyl, (1–6C)alkoxy, oxo, OH, COOH, CF₃, or halogen, and from (6–14C)aryl, (7–15C)aralkyl and (8–16C) aralkenyl, the aryl groups of which may be substituted with (1–6C)alkyl, (3–8C)cycloalkyl, (1–6C)alkoxy, OH, COOH, CF₃ or halogen; each group $R^2$ is independently H or has the same meaning as $R^1$, m is 1, 2 or 3;

B is a bond, an amino acid of the formula —NH—CH [(CH₂)ₚC(O)OH]—C—(O)— or an ester derivative thereof with p being 0, 1, 2 or 3, —N((1–12C)alkyl)—CH₂—CO—, —N((2–12C)alkenyl)—CH₂—CO—, —N((2–12C)alkynyl)—CH₂—CO—, —N(benzyl)CH₂—CO—, D-1-Tiq, D-3-Tiq, D-Atc, Aic, D-1-Piq, D-3-Piq or a L- or D-amino acid having a hydrophobic, basic or neutral side chain, which amino acid may be N-(1–6C)alkyl substituted;

or A and B together are residue $R^3R^4N$—CHR⁵—C(O)—, wherein $R^3$ and $R^4$ independently are $R^1$, $R^1$—O—C(O)—, $R^1$—C(O)—, $R^1SO_2$—, $R^2OOC$—(CHR²)ₘ—SO₂—, $R^2OOC$—(CHR²)ₘ—, H₂NCO—(CHR²)ₘ—, or an N-protecting group, or one of $R^3$ and $R^4$ is connected with $R^5$ to form a 5- or 6-membered ring together with "N—C" to which they are bound, which ring may be fused with an aliphatic or aromatic 6-membered ring; and $R^5$ is a hydrophobic, basic or neutral side chain;

X is an L-amino acid with a hydrophobic side chain, serine, threonine, a cyclic amino acid that may contain an additional heteroatom selected from N, O and S, and may be substituted with (1–6C)alkyl, (1–6C)alkoxy, benzyloxy or oxo, or X is —NR$^2$—CH$_2$—C(O)— or the fragment

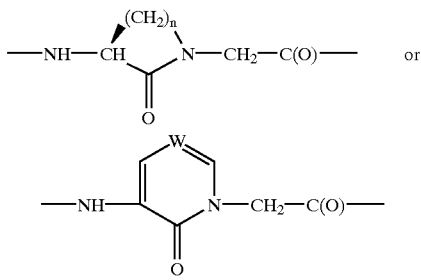

wherein n is 2, 3 or 4, and W is CH or N;
Y is H, —CHF$_2$, —CF$_3$, —CO—NH-(1–6C)alkylene-C$_6$H$_5$, —COOR$^6$ with R$^6$ being H or (1–6C)alkyl, —CONR$^7$R$^8$ with R$^7$ and R$^8$ being independently H or (1–6C)alkyl or R$^7$ and R$^8$ together being (3–6C)alkylene, or Y is a heterocycle selected from 2-thiazole, 2-thiazoline, 2-benzothiazole, 2-oxazole, 2-oxazoline and 2-benzoxazole, which heterocyles may be substituted with (1–6C)alkyl, phenyl, (1–6C)alkoxy, benzyloxy or oxo;
and r is 0, 1, 2 or 3;
or a compound of formula I, wherein the substituent variables are as defined above, and wherein the amino group of the alkynylamino side chain is protected with a substituent selected from the group consisting of hydroxy, (C$_{1-6}$)alkoxy, and (C$_{1-6}$) alkoxy carbonyl; or a salt thereof.

2. The compound of claim 1, wherein X is an L-amino acid with a hydrophobic side chain, serine, threonine or —NR$^2$—CH$_2$—C(O)—.

3. The compound of claim 1, wherein B is a bond, an amino acid of the formula
—NH—CH [(CH$_2$)$_p$C(O)OH]—C(O)— or an ester derivative thereof with p being 0, 1, 2 or 3, (—N((1–6C)alkyl)—CH$_2$ —CO—, -N(benzyl)CH$_2$—CO—, D-1-Tiq, D-3-Tiq, D-Atc, Aic, D-1-Piq, D-3-Piq or a D-amino acid having a hydrophobic, side chain, which amino acid may be N-(1–6C)alkyl substituted;
or A and B together are the residue R$^3$R$^4$N—CHR$^5$—C(O)—;
and X is a cyclic amino acid that may contain an additional heteroatom selected from N, O and S, and may be substituted with (1–6C)alkyl, (1–6C)alkoxy, benzyloxy or oxo, or X is —NR$^2$—CH$_2$—C(O)— or the fragment

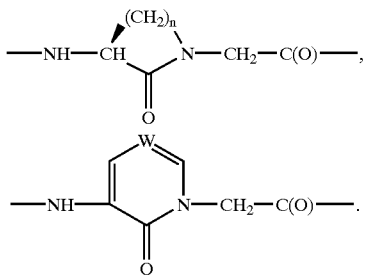

4. The compound of claim 3, wherein A is H, 2-hydroxy-3-cyclohexyl-propionyl-, 9-hydroxy-fluroene-9-carboxyl, R$^1$, R$^1$—SO$_2$—, R$^2$OOC—(CHR$^2$)$_m$—SO$_2$—, R$^2$OOC—(CHR$^2$)$_m$—, H$_2$NCO—(CHR$^2$)$_m$—, or an N-protecting group, wherein R$^1$ is selected from (1–12C)alkyl, (2–12C)alkenyl, (6–14C)aryl, (7–15C)aralkyl and (8–16C)aralkenyl; each group R$^2$ is independently H or has the same meaning as R$^1$;
B is a bond, D-1-Tiq, D-3-Tiq, D-Atc, Aic, D-1-Piq, D-3-Piq or a D-amino acid having a hydrophobic side chain, which amino acid may be N-(1–6C)alkyl substituted;
or A and B together are the residue R$^3$R$^4$N—CHR$^5$—C(O)—;
Y is —CO—NH-(1–6C)alkylene-C$_6$H$_5$, —COOR$^6$, —CONR$^7$R$^8$, or Y is a heterocycle selected from 2-thiazole, 2-thiazoline, 2-benzothiazole, 2-oxazole, 2-oxazoline and 2-benzoxazole.

5. The compound of claim 4, wherein A is H, R$^1$—SO$_2$— or R$^2$OOC—(CHR$^2$)$_m$—;
B is a bond, D-1-Tiq, D-3-Tiq, D-Atc, Aic, D-1-Piq, D-3-Piq or a D-amino acid having a hydrophobic side chain;
or A and B together are the residue R$^3$R$^4$N—CHR$^5$—C(O)—, wherein at least one of R$^3$ and R$^4$ is R$^2$OOC—(CHR$^2$)$_m$— or R$^1$—SO$_2$— and the other independently is (1–12C)alkyl, (2–12C)alkenyl, (2–12C)alkynyl, (3–8C)cycloalkyl, (7–15C)aralkyl, R$^1$—SO$_2$— or R$^2$OOC—(CHR$^2$)$_m$—, and R$^5$ is a hydrophobic side chain;
Y is —CO—NH-(1–6C)alkylene-C$_6$H$_5$, —COOR$^6$ with R$^6$ being H or (1–3C)alkyl, —CONR$^7$R$^8$ with R$^7$ and R$^8$ being independently H or (1–3C)alkyl or R$^7$ and R$^8$ together being (3–5C)alkylene, or Y is a heterocycle selected from 2-thiazole, 2-benzothiazole, 2-oxazole and 2-benzoxazole.

6. The compound of claim 5, wherein A is R$^2$OOC—(CHR$^2$)$_m$—;
B is a D-amino acid having a hydrophobic side chain;
or A and B together are the residue R$^3$R$^4$N—CHR$^5$—C(O)—, wherein at least one of R$^3$ and R$^4$ is R$^2$OOC—(CHR$^2$)$_m$— and the other independently is (1–12C)alkyl, (2–6C)alkenyl, (3–8C)cycloalkyl, benzyl, R$^1$—SO$_2$— or R$^2$OOC—(CHR$^2$)$_m$—;
and X is 2-azetidine carboxylic acid, proline, pipecolic acid, 4-thiazolidine carboxylic acid, 3,4-dehydroproline, 2-octahydroindole carboxylic acid or —[N(3–8C)cycloalkyl]-CH$_2$—C(O)—.

7. The compound of claim 6, wherein A is HOOC—CH$_2$—;
B is D-Phe, D-Cha, D-Coa, D-Dpa, p-Cl-D-Phe, p-OMethyl-D-Phe, p-OEthyl-D-Phe, D-Nle, m-Cl-D-Phe, 3,4-di-OMe-D-Phe, or D-Chg;
or A and B together are the residue R$^3$R$^4$N—CHR$^5$—C(O)—, wherein at least one of R$^3$ and R$^4$ is HOOC—CH$_2$— and the other independently is (1–4C)alkyl, (1–4C)alkyl-SO$_2$— or HOOC—CH$_2$— and
R$^5$ is (3–8C)cycloalkyl, (3–8C)cycloalkyl(1–4C)alkyl, phenyl, benzyl, that may be substituted with chlorine or (1–4C)alkoxy.

8. The compound of claim 7, wherein Y is a heterocycle selected from 2-thiazole, 2-benzothiazole, 2-oxazole and 2-benzoxazole.

9. The compound of claim 5, wherein A is R$^1$—SO$_2$—;
B is a bond, D-1-Tiq, D-3-Tiq, D-Atc, Aic, D-1-Piq, D-3-Piq or a D-amino acid having a hydrophobic side chain;
or A and B together are the residue R$^3$R$^4$N—CHR$^5$—C(O)—, wherein at least one of R$^3$ and R$^4$ is R$^1$—SO$_2$— and the other independently is (1–12C)alkyl or R$^1$—SO$_2$—;

X is 2-azetidine carboxylic acid, proline, pipecolic acid, 4-thiazolidine carboxylic acid, 3,4-dehydro-proline, 2-octahydroindole carboxylic acid, —[N(cyclopentyl)]-CH$_2$—C(O)— or the fragment

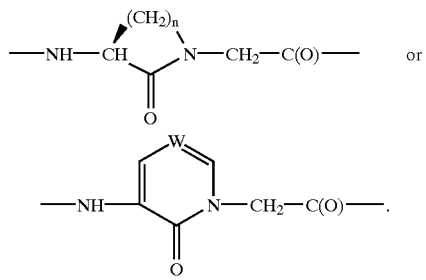

10. The compound of claim 9, wherein A is Ethyl-SO$_2$— or Benzyl-SO$_2$—;
   B is a bond, D-Phe, D-Cha, D-Coa, D-Dpa, p-Cl-D-Phe, p-OMethyl-D-Phe, p-OEthyl-D-Phe, D-Nle, m-Cl-D-Phe, 3,4-di-OMe-D-Phe, or D-Chg;
   or A and B together are the residue R$^3$R$^4$N—CHR$^5$—C(O)—, wherein at least one of R$^3$ and R$^4$ is Ethyl-SO$_2$13 or Benzyl-SO$_2$— and the other independently is (1–12C)alkyl or R$^1$—SO$_2$— and R$^5$ is (3–8C)cycloalkyl, (3–8C)cycloalkyl(1–4C)alkyl, phenyl, benzyl, diphenylmethinyl, which groups may be substituted with chlorine or (1–4C)alkoxy.

11. The compound of claim 10, wherein Y is —CO—NH—CH$_2$C$_6$H$_5$, —CO—NH—CH$_2$CH$_2$C$_6$H$_5$ or —CONR$^7$R$^8$, R$^7$ and R$^8$ being independently H or (1–3C)alkyl or with R$^7$ and R$^8$ together being (3–5C)alkylene, or Y is a heterocycle selected from 2-thiazole, 2-benzothiazole, 2-oxazole and 2-benzoxazole.

12. The compound of claim 1, wherein r is 1.

13. A composition comprising the compound of claim 1 in an amount sufficient to inhibit a serine protease, and a suitable carrier.

14. A method for preparing a composition, comprising admixing a compound according to claim 1, in an amount sufficient to inhibit a serine protease, with a suitable carrier.

15. A method for inhibiting thrombin in a mammal suffering from myocardial infarction comprising administering to said mammal a compound of claim 1 for a time and under conditions effective to inhibit thrombin.

16. A method for inhibiting thrombin in a mammal afflicted with pulmonary embolism comprising administering to said mammal a compound of claim 1 for a time and under conditions effective to inhibit thrombin.

17. A method of inhibiting thrombin comprising administering to a mammal in need thereof a compound of claim 1 for a time and under conditions effective to inhibit thrombin.

* * * * *